United States Patent
Paranhos-Baccala et al.

(12) 
(10) Patent No.: US 6,403,103 B1
(45) Date of Patent: *Jun. 11, 2002

(54) TRYPANOSOMA CRUZI ANTIGEN, GENE ENCODING THEREFORE, AND METHODS OF DETECTING AND TREATING CHAGAS DISEASE

(75) Inventors: Glaucia Paranhos-Baccala, Lyons; Mylene Lesenechal, Villeurbanne; Michel Jolivet, Bron; Bernard Mandrand, Villeurbanne, all of (FR)

(73) Assignee: Bio Merieux, Marcy l'Etoile (FR)

( * ) Notice: Subject to any disclaimer, the term of this patent is extended or adjusted under 35 U.S.C. 154(b) by 0 days.

This patent is subject to a terminal disclaimer.

(21) Appl. No.: 08/988,242

(22) Filed: Dec. 10, 1997

Related U.S. Application Data

(63) Continuation-in-part of application No. 08/480,917, filed on Jun. 7, 1995, now Pat. No. 5,820,864.

(30) Foreign Application Priority Data

Aug. 12, 1995 (FR) .............................................. 94 10132

(51) Int. Cl.7 ............................................. A61K 39/002
(52) U.S. Cl. ................................ 424/269.1; 424/185.1; 424/190.1; 424/193.1; 424/265.1; 530/350; 530/387.1; 530/387.2; 530/387.9; 530/388.6; 435/7.1

(58) Field of Search .............................. 530/350, 387.1, 530/387.2, 387.9, 388.6; 424/185.1, 193.1, 190.1, 265.1, 269.1; 435/6, 7.1

(56) References Cited

FOREIGN PATENT DOCUMENTS

WO    WO 96/05312    2/1996

OTHER PUBLICATIONS

Pyrc et al. Gencore Accession No. A42170, 1992.*
Kennedy et al. Gencore Accession No. B47236, 1992.*
Jacobson et al. Gencore Accession No. R22382, 1992.*
Geysen et al. J. Molec. Recog. 1988. 1(1): 32–42, 1988.*

* cited by examiner

Primary Examiner—Jennifer E. Graser
(74) Attorney, Agent, or Firm—Oliff & Berridge, PLC

(57) ABSTRACT

The nucleotide sequence of Tc100, a gene encoding a new antigenic protein from *Trypanosoma cruzi* called PTc100, is disclosed. The amino acid sequence of the PTc100 protein is also disclosed, along with the amino acid sequence of the dominant antigenic epitope of the PTc100 protein. The PTc100 protein and Tc100 gene, or a fragment thereof, modified or otherwise, can be used directly or indirectly for the detection of *Trypanosoma cruzi*, or for the monitoring of an infection generated by *T. cruzi* in man or animals.

18 Claims, 10 Drawing Sheets

FIG 5
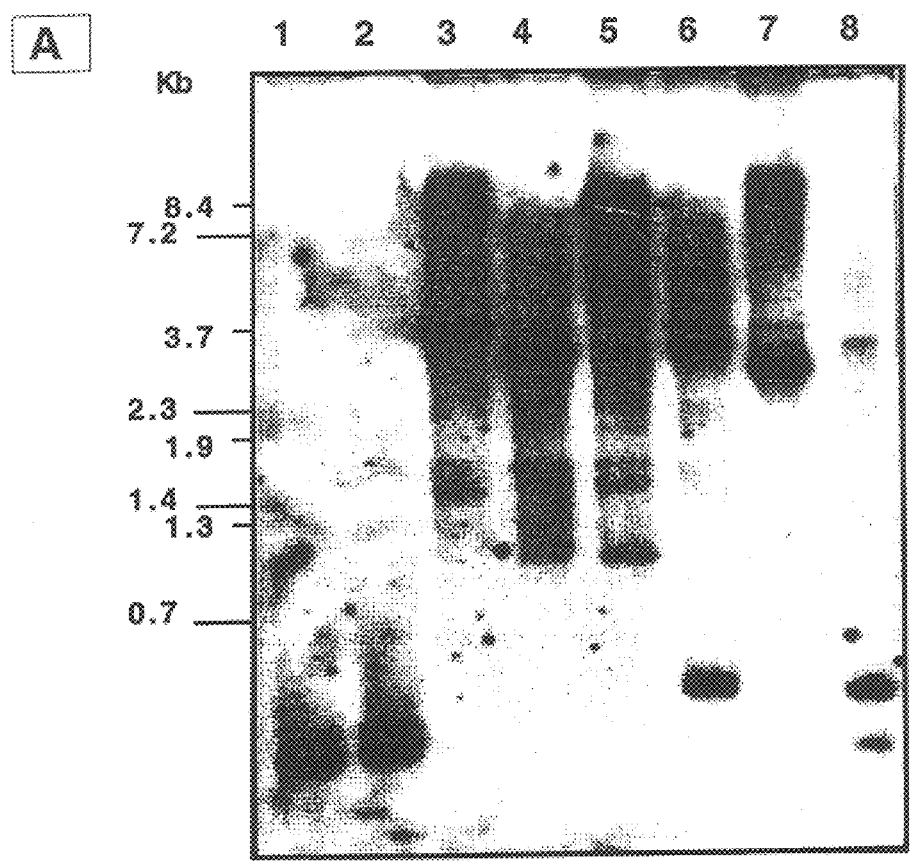
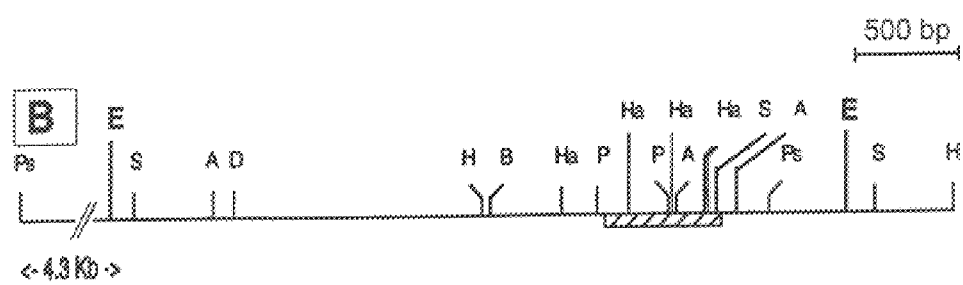

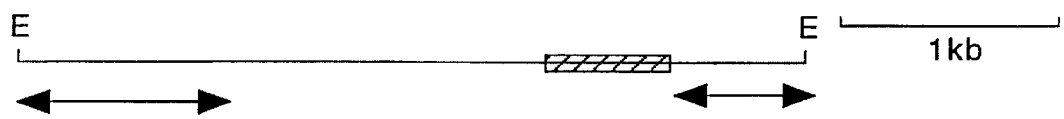

B

```
AATTCTTGCTTGTTATTATTGCTGATGCTGCTATTGCGAATCGTACATATGTATGCATGCATGTATGTACAAATATT    80
                                                        M  H  A  C  M  Y  K  Y
TAGGAATTTATCTATACCCTGTTAGAGCTCCTGACGCCTCCCATCCCCTTTTTTTTGTTTTTTGCATTCTCCTTCTC   160
 L  G  I  Y  L  Y  P  V  R  A  P  D  A  S  H  P  L  F  F  V  F  C  I  L  L  L
CTCTCAGTCTCTCTCTCTCTCTCTCTGTGTGTGTGTGTGGGTGTTGTCGTGTGCTCATTTGTACATTTTGAACGT   240
  L  S  V  S  L  S  L  S  L  C  V  C  V  W  V  L  S  C  A  H  L  Y  I  L  N  V
TGGGAGGATGGGAGGCGTCAGATTTGTCCTTTTTCCTTTTTTTTTTTGTGTGTGTGTTTGTGTTTCCACCCTTTTA   320
   G  R  M  G  G  V  R  F  V  L  P  P  F  F  F  L  C  V  C  L  C  F  H  P  F
ATTTTTGCGGAGAAAAGAGAGAGAGAGAAGGGGCGGAGGGGGACACGCATTGCAGTTGTGTAAATGACATTGCCTC   400
  Y  F  C  G  E  K  R  E  R  E  G  A  E  G  G  H  A  L  Q  L  C  K  *
GTGATGTTGCATGCATGCATGCGTACATGCACATGCACATATCTATCTATATATATATATATATATAACGAGAGGGA   480
AACGAGGAGTAGGGAGGGGGAGAGGGATTCATTTCATATTCAGTTAATCTGTGCACACATGGTATACAAATGCGCC   560
AGACAAGGCGTCCGAGCAATATATATATATATAAATTATATTCTTGTTTAAATTTAAATTAAATATATAAATACAGGAG   640
                                     ┗━━━→ +1
AAGGTGGTGGAGGTGGAAGAGAGGGGATTGGGGGAAAGAATGAAAATGTTGGAAGGAATAATGGGGGAAATTGTAGG   720
ATTGCTGTTGTTGTTGTTTTTGCTGCTTCACCGAGCGTTTCCCTGTTGTTGTTGTTGTCGTTTCTTTTTTTTTTGGT   800
TTGGTTTTTTTTTGNGTNTTTATNAATNCANNANAGNGTTTCCNNTNNTCTCTCTCTNNCCCNGNCGNTCNCTCTCT   880
TNTGTGTNTGTGTGCANANNTNTNGAGNTATCCCCNGGNANTTCTNTTTTTTTTTTTGGGGGATGGNGGGGGGNCT   960
NTTGNCTCCNNNGGTGTCAANNNGCGGCGNGCTATTNTTACAGNAG                                1023
```

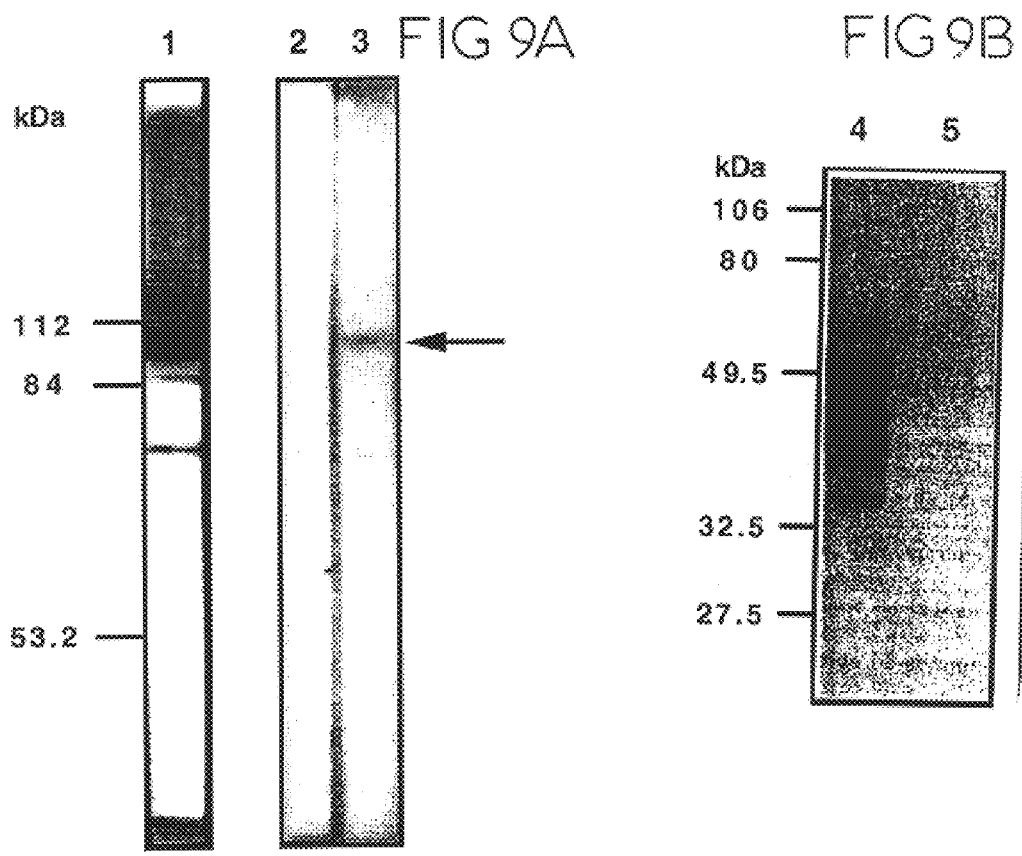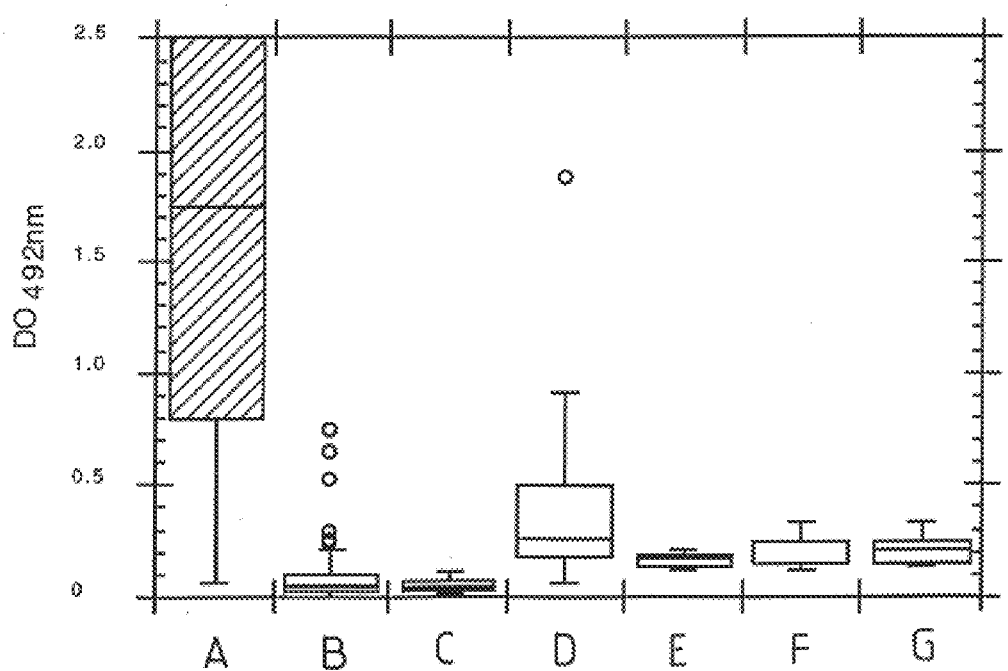

SEQUENCE LISTING (1) GENERAL INFORMATION:

(iii) NUMBER OF SEQUENCES: 19

(2) INFORMATION FOR SEQ ID NO:1:

(i) SEQUENCE CHARACTERISTICS:
       (A) LENGTH: 3402 base pairs
       (B) TYPE: nucleic acid
       (C) STRANDEDNESS: double
       (D) TOPOLOGY: linear (ii) MOLECULE TYPE: cDNA (xi) SEQUENCE DESCRIPTION: SEQ ID NO:1:

```
AACGCTATTA TTAGAACAGT TTCTGTACTA TATTGTCATT TGGGGAGGGG G GAAAGGGGG      60
GAAGTACTTG CCGTTTTGTG TGGGTGACGA GACAACACAC ATCGAGCGGG A AGAAAAAAA    120
AAAAGGAAAT AAATTAAATT AAATTATTTG TTCTTTGAAT AGGCAAAGAA G AAGAAGAAG    180
AAAAGGTGCG GGGGAGGGAG GAGAAAGCGA CACACACACA AAAAAAAAAA A AGGAATTGC    240
GGAAATAACA ACGCAAGGCG CGGACATGAC CGTGACGGTG GATTTGTTCA A TCATGCGAA    300
GCCGAGCAAC AATGAGGGCC GCGTGTGGTC TGTGGACGCC GCGACATTTA A CGAGGTGCC    360
TGAGGCGCAG CGTGTGCTGG CGGATTCGCA GTTTTATCTT GCCTACACCA T GAAGCGGCG    420
TCACGTGCTG CGTGTGGTGA AGCGCTCGAA CCTTTTGAAG GGCACCGTGC G GGCACACTC    480
AAAGCCCATT CATGCGGTGA AGTTTGTGAA TTACCGCAGT AACGTCGCAG C ATCGGCTGG    540
GAAGGGGAG TTCTTCGTGT GGGTTGTGAC GGATGAAACG GAGGCGAGCA A CGGCAAGCC    600
GGATCTCGCA GCCCGCCTCA CAGTGAAGGT GTACTTTAAG CTTCAGGATC C TGTCACAAT    660
TCCATGCTTT TCTTTCTTTA TCAACGCCGA GAGTCAGCGG CCTGATCTGC T TGTCCTTTA    720
CGAAACGCAG GCGGCAATTC TTGACAGCTC CTCCCTCATT GAGCGCTTTG A CGTGGAATC    780
ACTGGAGGCA ACACTACAGC GGAATTGCAC AACCCTGCGA ACCCTGACTC A ACCGGTTAG    840
TGAGAACAGT TTATGCTCCG TTGGCTCTGG CGGATGGTTC ACCTTTACCA C GGAACCAAC    900
AATGGTAGCG GCATGCACAT TACGAAACCG CAGCACTCCA TCATGGGCGT G TTGCGAGGG    960
TGAGCCAGTG AAGGCATTGC ATCTCCTTGA CGCAACCGTT GAGGAAAATG T CAGTGTTCT   1020
CGTGGCCGCA TCTACAAAAG GGGTGTACCA ATGGCTCCTT ACGGGTGTAG C AGAACCAAA   1080
CTTGTTGCGC AAGTTTGTCA TTGATGGATC TATTGTCGCG ATGGAAAGCT C ACGAGAAAC   1140
GTTTGCCGTG TTTGACGACA GGAAGCAGCT GGCGCTGGTC AACATGCATT C CCCTCATAA   1200
CTTTACCTGC ACACACTACA TGATGCCTTG TCAGGTACAG CGTAACGGCT T TTGCTTCAA   1260
TCGTACAGCC GACGGTAGCT GCGTCCTGGC TGACATGTCG ATTCGATTGA C GATCTTCCA   1320
TCTCCGGTCC TCCCGCAGGG AAGAACAGCA GCCAGGCCAA AAAACATCGG T AGTGGCGAC   1380
GGCGAAACCG GGGTGTGTGT CCTCGGGCAC TGACGCGGCG AGTAGCAGTC A TACCAATAC   1440
GACTTCTGCC GCTGCTGCAT CCCCTGCATC ACCCCCTGTT TCAGCGCCAG C CAAGGCAGC   1500
CGCGCCTCCT GCCGCGGCGC GATCGGCTGA GCCGCACGTG GGGAGCAAGA T CATTGCTAA   1560
TCTAGTGAAT CAGCTGGGGA TTAATGTCAC CCAAAGGAGC GTCGTCAGCA C TGGAGCGCC   1620
GGCCACGACG AGGTCTACGG CGGTGACGTC CACGACTACC GCCCCGCAGC G AACAAGTCC   1680
ATACGGGCAC AATGGCCGAC CTGTGACGGC TGGATTGGTG GCAGCTAATA G TGGTGCCAG   1740
CGCGGCCTCG TCTCCCACAG CCGCGGCGAA ACCAACAGGA GAAGAAAAGG C CTCCGCGGC   1800
```

-continued

```
ATGTGAAACG AGCTCCGTGG CGATAAATGC GACACGCCCG GCGCTTCACA A CGCCTCTCT      1860

CCCGCAGGCG CCAACGGATG GCGTTTTGGC GGCAGCAGTA TACCAGTCGG A GGGCGAGGT      1920

TCATCAGTCG CTGGAGCGGC TGGAGTCCGT CATAACCAAC ACGTCTCGGG T TCTGAAGTT      1980

GCTCCCTGAC ACCATTCGAA GAGACCATGA ACAACTTCTG AATCTGGGTT T AGAGGCACA      2040

GATGACAGAG CTGCAGCAGA GCCGTCCAAC ACCGCAAACA CAGCCGAGAG A CACAAGCTC      2100

CGCGAAATCA TCCGTGTTTG AGACGTACAC CCTTGTTCTC ATTGCGGATT C CCTCTCTCG      2160

CAACATCACG AAGGGGTGA AGCGTGGTGT GAACGAGGCC ATTATGTTGC A TCTCGACCA       2220

TGAGGTGCGG CACGCCATAG GAACCGGCT TCGGCAAACA CAAAGAACA T CATCAAGAG        2280

CCGCCTCGAT GAAGCGTTGA AGGAAAGCAC TACACAGTTT ACGGCTCAAT T GACGCAAAC     2340

GGTGGAGAAT CTGGTGAAGC GCGAGCTTGC CGAGGTGCTT GGTAGCATCA A CGGCTCCCT     2400

CACTTCTCTC GTGAAGGAAA ATGCCTCATT ACAGAAAGAG TTGAATTCCA T AATGTCTAG     2460

TGGGGTGTTG GATGAAATGC GTCGTATGCG GGAAGAGCTG TGCACATTGC G AGAGTCCGT    2520

TGCGAAGCGG AAGGCAACAA TGCCAGATTC TTCTCTTCAC GCCACGAGCT C CTTTCAAGG    2580

AAGAAGGTCT GCGCCCGAGA CAATTCTTGC AACCGCGTTA TCGATGGTGC G AGAGCAGCA   2640

ATACCGTCAG GGACTGGAAT ACATGTTGAT GGCTCAGCAG CCCTCTCTCC T CCTGCGGTT   2700

CCTCAGCATA CTTACAAGGG AAAACGAAAA CGCCTACTCG GAACTTATTG A AAATGTAGA   2760

GACGCCGAAT GACGTGTGGT GTTCGGTTCT GTTGCAACTC ATAGAGGCCG C GGCGACCGA   2820

GGCTGAGAAG GAGGTGGTTG TTGGCGTCGC CATTGATATT CTCTCCGAGC G CGATCAAAT   2880

TGCTCAGAAC GGCGCACTCG GCTCGAAACT CACCACCGCC ATGCGAGCCT T TGAGCGACA   2940

GGCAAGGTCG GAGACAACGA GCAGGTCATT CTTGCAATGC CTGAAGAACC T GGAAAAGCT   3000

TCTGCAATCA TGATAATAAA AAGAACTCAA CGAATACAGT TGTTGATTAT T AAGGAAGGG   3060

AAAAGAGAGA AAGAGAGAGA GAGAGAGAGA AATGTAATGG GCGTTTAGTT A CGGTAGAAA   3120

GAAAACGTGT GGATAAGAAG GAGGGGTTTT GTGTGCGACC AGGAATTACT G GGGAACGCT   3180

GCTACACGGC GGAATCGACC ATTTTATTAT TATTATTATT GTCTTTAGTA T TATGTTTTT   3240

TCTTGTGTGT GTGTGTGTGT GTTTGTGTGT GTGCGGTTAT TTTGTATCCG T TTGCTCCCG   3300

CCCCTGCCCC CCATCACCCG AGGAGAAAGT AGAATAAGAC ACATACGATT G TTGTTTTG    3360

TTATCCTTAA AAGGAAGAGA GACCAAAAAA AAAAAAAAAA AA                        3402
```

(2) INFORMATION FOR SEQ ID NO:2:

(i) SEQUENCE CHARACTERISTICS:
        (A) LENGTH: 915 amino acids
        (B) TYPE: amino acid
        (C) STRANDEDNESS: single
        (D) TOPOLOGY: linear (ii) MOLECULE TYPE:
        (A) DESCRIPTION: /desc = "protein"

(xi) SEQUENCE DESCRIPTION: SEQ ID NO:2:

```
Met Thr Val Thr Val Asp Leu Phe Asn His A la Lys Pro Ser Asn Asn
1               5                  10                  15

Glu Gly Arg Val Trp Ser Val Asp Ala Ala T hr Phe Asn Glu Val Pro
            20                  25                  30

Glu Ala Gln Arg Val Leu Ala Asp Ser Gln P he Tyr Leu Ala Tyr Thr
        35                  40                  45

Met Lys Arg Arg His Val Leu Arg Val Val L ys Arg Ser Asn Leu Leu
    50                  55                  60
```

-continued

```
Lys Gly Thr Val Arg Ala His Ser Lys Pro Ile His Ala Val Lys Phe
 65                  70                  75                  80

Val Asn Tyr Arg Ser Asn Val Ala Ala Ser Ala Gly Lys Gly Glu Phe
                 85                  90                  95

Phe Val Trp Val Val Thr Asp Glu Thr Asp Ala Ser Asn Gly Lys Pro
            100                 105                 110

Asp Leu Ala Ala Arg Leu Thr Val Lys Val Tyr Phe Lys Leu Gln Asp
            115                 120                 125

Pro Val Thr Ile Pro Cys Phe Ser Phe Phe Ile Asn Ala Glu Ser Gln
        130                 135                 140

Arg Pro Asp Leu Leu Val Leu Tyr Glu Thr Gln Ala Ala Ile Leu Asp
145                 150                 155                 160

Ser Ser Ser Leu Ile Glu Arg Phe Asp Val Glu Ser Leu Glu Ala Thr
                165                 170                 175

Leu Gln Arg Asn Cys Thr Thr Leu Arg Thr Leu Thr Gln Pro Val Ser
            180                 185                 190

Glu Asn Ser Leu Cys Ser Val Gly Ser Gly Gly Trp Phe Thr Phe Thr
            195                 200                 205

Thr Glu Pro Thr Met Val Ala Ala Cys Thr Leu Arg Asn Arg Ser Thr
        210                 215                 220

Pro Ser Trp Ala Cys Cys Glu Gly Glu Pro Val Lys Ala Leu His Leu
225                 230                 235                 240

Leu Asp Ala Thr Val Glu Glu Asn Val Ser Val Leu Val Ala Ala Ser
                245                 250                 255

Thr Lys Gly Val Tyr Gln Trp Leu Leu Thr Gly Val Ala Glu Pro Asn
            260                 265                 270

Leu Leu Arg Lys Phe Val Ile Asp Gly Ser Ile Val Ala Met Glu Ser
            275                 280                 285

Ser Arg Glu Thr Phe Ala Val Phe Asp Asp Arg Lys Gln Leu Ala Leu
        290                 295                 300

Val Asn Met His Ser Pro His Asn Phe Thr Cys Thr His Tyr Met Met
305                 310                 315                 320

Pro Cys Gln Val Gln Arg Asn Gly Phe Cys Phe Asn Arg Thr Ala Asp
                325                 330                 335

Gly Ser Cys Val Leu Ala Asp Met Ser Asn Arg Leu Thr Ile Phe His
            340                 345                 350

Leu Arg Cys Ser Arg Arg Glu Glu Gln Gln Pro Gly Gln Lys Thr Ser
            355                 360                 365

Val Val Ala Thr Ala Lys Pro Gly Cys Val Ser Ser Gly Thr Asp Ala
        370                 375                 380

Ala Ser Ser Ser His Thr Asn Thr Thr Ser Ala Ala Ala Ala Ser Pro
385                 390                 395                 400

Ala Ser Pro Pro Val Ser Ala Pro Ala Lys Ala Ala Ala Pro Pro Ala
                405                 410                 415

Ala Ala Arg Ser Ala Glu Pro His Val Gly Ser Lys Ile Ile Ala Asn
            420                 425                 430

Leu Val Asn Gln Leu Gly Ile Asn Val Thr Gln Arg Ser Val Val Ser
            435                 440                 445

Thr Gly Ala Pro Ala Thr Thr Arg Ser Thr Ala Val Thr Ser Thr Thr
        450                 455                 460

Thr Ala Pro Gln Arg Thr Ser Pro Tyr Gly His Asn Gly Arg Pro Val
465                 470                 475                 480
```

```
Thr Ala Gly Leu Val Ala Ala Asn Ser Gly Ala Ser Ala Ala Ser Ser
                485                 490                 495

Pro Thr Ala Ala Ala Lys Pro Thr Gly Glu Glu Lys Ala Ser Ala Ala
            500                 505                 510

Cys Glu Thr Ser Ser Val Ala Ile Asn Ala Thr Arg Pro Ala Leu His
            515                 520                 525

Asn Ala Ser Leu Pro Gln Ala Pro Thr Asp Gly Val Leu Ala Ala Ala
            530                 535                 540

Val Tyr Gln Ser Glu Gly Glu Val His Gln Ser Leu Glu Arg Leu Glu
545                 550                 555                 560

Ser Val Ile Thr Asn Thr Ser Arg Val Leu Lys Leu Leu Pro Asp Thr
            565                 570                 575

Ile Arg Arg Asp His Glu Gln Leu Leu Asn Leu Gly Leu Glu Ala Gln
            580                 585                 590

Met Thr Glu Leu Gln Gln Ser Arg Pro Thr Pro Gln Thr Gln Pro Arg
            595                 600                 605

Asp Thr Ser Ser Ala Lys Ser Ser Val Phe Glu Thr Tyr Thr Leu Val
            610                 615                 620

Leu Ile Ala Asp Ser Leu Ser Arg Asn Ile Thr Lys Gly Val Lys Arg
625                 630                 635                 640

Gly Val Asn Glu Ala Ile Met Leu His Leu Asp His Glu Val Arg His
            645                 650                 655

Ala Ile Gly Asn Arg Leu Arg Gln Thr Gln Lys Asn Ile Ile Lys Ser
            660                 665                 670

Arg Leu Asp Glu Ala Leu Lys Glu Ser Thr Thr Gln Phe Thr Ala Gln
            675                 680                 685

Leu Thr Gln Thr Val Glu Asn Leu Val Lys Arg Glu Leu Ala Glu Val
            690                 695                 700

Leu Gly Ser Ile Asn Gly Ser Leu Thr Ser Leu Val Lys Glu Asn Ala
705                 710                 715                 720

Ser Leu Lys Lys Glu Leu Asn Ser Ile Met Ser Ser Gly Val Leu Asp
            725                 730                 735

Glu Met Arg Arg Met Arg Glu Glu Leu Cys Thr Leu Arg Glu Ser Val
            740                 745                 750

Ala Lys Arg Lys Ala Thr Met Pro Asp Ser Ser Leu His Ala Thr Ser
            755                 760                 765

Ser Phe Gln Gly Arg Arg Ser Ala Pro Glu Thr Ile Leu Ala Thr Ala
            770                 775                 780

Leu Ser Met Val Arg Glu Gln Gln Tyr Arg Gln Gly Leu Glu Val Met
785                 790                 795                 800

Leu Met Ala Gln Gln Pro Ser Leu Leu Leu Arg Phe Leu Ser Ile Leu
            805                 810                 815

Thr Arg Glu Asn Glu Asn Ala Tyr Ser Glu Leu Ile Glu Asn Val Glu
            820                 825                 830

Thr Pro Asn Asp Val Trp Cys Ser Val Leu Leu Gln Leu Ile Glu Ala
            835                 840                 845

Ala Ala Thr Glu Ala Glu Lys Glu Val Val Val Gly Val Ala Ile Asp
            850                 855                 860

Ile Leu Ser Glu Arg Asp Gln Ile Ala Gln Asn Gly Ala Leu Gly Ser
865                 870                 875                 880

Lys Leu Thr Thr Ala Met Arg Ala Phe Glu Arg Gln Ala Arg Ser Glu
            885                 890                 895
```

```
Thr Thr Ser Arg Ser Phe Leu Gln Cys Leu Lys Asn Leu Ile Lys Leu
        900                 905                 910

Leu Gln Ser
        915
```

(2) INFORMATION FOR SEQ ID NO:3:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

```
AACGCTATTA TTAGAACAGT T                                              21
```

(2) INFORMATION FOR SEQ ID NO:4:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

```
TGCAGCAGCG GCAGAAGT                                                  18
```

(2) INFORMATION FOR SEQ ID NO:5:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

```
CAGCCGACGG TAGCTGCGTC CT                                             22
```

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

```
ACATAATGGC CTCGTTCACA C                                              21
```

(2) INFORMATION FOR SEQ ID NO:7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

CGAAGAGACC ATGAACAACT T                                                    21

(2) INFORMATION FOR SEQ ID NO:8:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE:
        (A) DESCRIPTION:/desc = "protein"

(xi) SEQUENCE DESCRIPTION: SEQ ID NO:8:

Ser Pro Pro Val Ser Ala Pro Ala Lys Ala
1               5                   10

(2) INFORMATION FOR SEQ ID NO:9:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE:
        (A) DESCRIPTION:/desc = "protein"

(xi) SEQUENCE DESCRIPTION: SEQ ID NO:9:

Pro Val Ser Ala Pro Ala Lys Ala Ala Ala
1               5                   10

(2) INFORMATION FOR SEQ ID NO:10:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE:
        (A) DESCRIPTION:/desc = "protein"

(xi) SEQUENCE DESCRIPTION: SEQ ID NO:10:

Ser Ala Pro Ala Lys Ala Ala Ala Pro Pro A la Ala
1               5                   10

(2) INFORMATION FOR SEQ ID NO:11:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE:
        (A) DESCRIPTION:/desc = "protein"

(xi) SEQUENCE DESCRIPTION: SEQ ID NO:11:

Pro Ala Lys Ala Ala Ala Pro Pro Ala Ala
1               5                   10

(2) INFORMATION FOR SEQ ID NO:12:

(i) SEQUENCE CHARACTERISTICS:
        (A) LENGTH: 10 amino acids
        (B) TYPE: amino acid (C) STRANDEDNESS: single
        (D) TOPOLOGY: linear (ii) MOLECULE TYPE:
        (A) DESCRIPTION:/desc = "protein"

(xi) SEQUENCE DESCRIPTION: SEQ ID NO:12:

Lys Ala Ala Ala Pro Pro Ala Ala Ala Arg
1               5                   10

(2) INFORMATION FOR SEQ ID NO:13:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE:
        (A) DESCRIPTION: /desc = "protein"

(xi) SEQUENCE DESCRIPTION: SEQ ID NO:13:

Ala Ala Pro Pro Ala Ala Ala Arg Ser Ala
1               5                   10

(2) INFORMATION FOR SEQ ID NO:14:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE:
        (A) DESCRIPTION: /desc = "protein"

(xi) SEQUENCE DESCRIPTION: SEQ ID NO:14:

Pro Pro Ala Ala Ala Arg Ser Ala Glu Pro H is Val
1               5                   10

(2) INFORMATION FOR SEQ ID NO:15:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE:
        (A) DESCRIPTION: /desc = "protein"

(xi) SEQUENCE DESCRIPTION: SEQ ID NO:15:

Ala Ala Ala Arg Ser Ala Glu Pro His Val
1               5                   10

(2) INFORMATION FOR SEQ ID NO:16:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: other nucleic acid
        (A) DESCRIPTION: /desc = "protein"

(xi) SEQUENCE DESCRIPTION: SEQ ID NO:16:

Ala Arg Ser Ala Glu Pro His Val Gly
1               5

(2) INFORMATION FOR SEQ ID NO:17:

(i) SEQUENCE CHARACTERISTICS:
        (A) LENGTH: 1006 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

```
AATTCTTGCT TGTTATTATT GCTGATGCTG CTATTGCGAA TCGTACATAT G TATGCATGC      60

ATGTATGTAC AAATATTTGT TAGGAATTTA TCTATACCCT GTTAGAGCTC C TGACGCCTC    120

CCATCCCCTT TTTTTTGTTT TTTGCATTCT CCTTCTCTTT CTCTCAGTCT C TCTCTCTCT    180

CTCTCTCTGT GTGTGTGTGT GGGTGTTGTC GTGTGCTCAT TTGTACATTT T GAACGTTGC    240

TGGGAGGATG GGAGGCGTCA GATTTGTCCT TTTTCCTTTT TTTTTTTTGT G TGTGTGTTT    300

GTGTTTCCAC CCTTTTATTT ATTTTTGCGG AGAAAAGAGA GAGAGAGAAG G GGCGGAGGG    360

GGGACACGCA TTGCAGTTGT GTAAATGACA TTGCCTCGCA GTGATGTTGC A TGCATGCAT    420

GCGTACATGC ACATGCACAT ATCTATCTAT ATATATATAT ATATATAACG A GAGGGAGAG    480

AACGAGGAGT AGGGAGGGGG AGAGGGATTC ATTTCATATT CAGTTAATCT G TGCACACAT    540

GGTATACAAA TGCGGCCATA AGACAAGGCG TCCGAGCAAT ATATATATAT A AATTATATT    600

CTTGTTTAAA TTTAAATTAA ATATATAAAT ACAGGAGGGG AAGGTGGTGG A GGTGGAAGA    660

GAGGGGATTG GGGGAAAGAA TGAAAATGTT GGAAGGAATA ATGGGGGAAA T TGTAGGAAA    720

ATTGCTGTTG TTGTTGTTTT TGCTGCTTCA CCGAGCGTTT CCCTGTTGTT G TTGTTGTCG    780

TTTCTTTTTT TTTTGGTTGG TTGGTTTTTT TTTGNGTNTT TATNAATNCA N NANAGNGTT    840

TCCNNTNNTC TCTCTCTNNC CCNGNCGNTC NCTCTCTCTC TNTGTGTNTG T GTGCANANN    900

TNTNGAGNTA TCCCCNGGNA NTTCTNTTTT TTTTTTTTGG GGGATGGNGG G GGGNCTTNT    960

NTTGNCTCCN NNGGTGTCAA NNNGCGGCGN GCTATTNTTA CAGNAG           1006
```

(2) INFORMATION FOR SEQ ID NO:18:

(i) SEQUENCE CHARACTERISTICS:
        (A) LENGTH: 107 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:18:

```
Met His Ala Cys Met Tyr Lys Tyr Leu Gly I le Tyr Leu Tyr Pro Val
1               5                   10                  15

Arg Ala Pro Asp Ala Ser His Pro Leu Phe P he Val Phe Cys Ile Leu
            20                  25                  30

Leu Leu Leu Ser Val Ser Leu Ser Leu Ser L eu Cys Val Cys Val Trp
        35                  40                  45

Val Leu Ser Cys Ala His Leu Tyr Ile Leu A sn Val Gly Arg Met Gly
    50                  55                  60

Gly Val Arg Phe Val Leu Phe Pro Phe Phe P he Leu Cys Val Cys Leu
65                  70                  75                  80

Cys Phe His Pro Phe Tyr Phe Cys Gly Glu L ys Arg Glu Arg Glu Gly
                85                  90                  95

Ala Glu Gly Gly His Ala Leu Gln Leu Cys L ys
            100                 105
```

-continued (2) INFORMATION FOR SEQ ID NO:19:

(i) SEQUENCE CHARACTERISTICS:
        (A) LENGTH: 198 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:19:

```
Gln Val Gln Arg Asn Gly Pro Cys Phe Asn A rg Thr Ala Asp Gly Ser
1               5                   10                  15

Cys Val Leu Ala Asp Asn Ser Asn Arg Leu T hr Ile Phe His Leu Ala
                20                  25                  30

Ser Ser Arg Arg Glu Glu Gln Pro Gly G ln Lys Thr Ser Val Val
            35                  40                  45

Ala Thr Ala Lys Pro Gly Cys Val Ser Ser G ly Thr Asp Ala Ala Ser
            50                  55                  60

Ser Ser Met Thr Asn Thr Thr Ser Ala Ala A la Ala Ser Pro Ala Ser
65                  70                  75                  80

Pro Pro Val Ser Ala Pro Ala Lys Ala Ala A la Pro Pro Ala Ala Ala
                85                  90                  95

Arg Ser Ala Glu Pro His Val Gly Ser Lys I le Ile Ala Asn Leu Val
                100                 105                 110

Asn Gln Leu Gly Ile Asn Val Thr Gln Arg S er Val Val Ser Thr Gly
            115                 120                 125

Ala Pro Ala Thr Thr Arg Ser Thr Ala Val T hr Ser Thr Thr Thr Ala
            130                 135                 140

Pro Gln Arg Thr Ser Pro Tyr Gly His Asn G ly Arg Pro Val Thr Ala
145                 150                 155                 160

Gly Leu Val Ala Ala Asn Ser Gly Ala Ser A la Ala Ser Ser Pro Thr
                165                 170                 175

Ala Ala Ala Lys Pro Thr Gly Glu Glu Lys A la Ser Ala Ala Cys Glu
            180                 185                 190

Thr Ser Ser Val Ala Ile
            195
```

TRYPANOSOMA CRUZI ANTIGEN, GENE ENCODING THEREFORE, AND METHODS OF DETECTING AND TREATING CHAGAS DISEASE

This application is a Continuation-In-Part of application Ser. No. 08/480,917, filed Jun. 7, 1995, now U.S. Pat. No. 5,820,864. The entire disclosure of the prior application is hereby incorporated by reference herein in its entirety.

FIELD OF THE INVENTION

The subject of the present invention is a new genetic material encoding a new protein and its fragments and its antigenic determinant recognized by anti-*Trypanosoma cruzi* antisera, and it relates to promoter sequence and to the use of said gene and protein and/or antigenic determinant, especially for diagnostic, pharmaceutical and therapeutic purposes.

BACKGROUND OF THE INVENTION

*Trypanosoma cruzi* is a flagellate protozoan parasite, a member of the order Kinetoplastida and of the family Trypanosomatidae, which is responsible for Chagas' disease which affects naturally millions of persons, mainly in Latin America.

In vertebrate hosts, *Trypanosoma cruzi* is present in two forms: one which is mobile by means of its flagellum or trypomastigote and which does not divide; the other is aflagellate, or intracellular amastigote, which multiplies by binary division.

Transmission of the protozoan in man occurs through hematophagous insects of the family Reduviidae, during a blood meal followed by dejections at the site of the bite. The vector insect thus releases the infectious metacyclic trypomastigote forms which will colonize many cell types through the blood circulation. *Trypanosoma cruzi* infects cardiac and skeletal muscle cells, glial cells, and cells of the mononuclear phagocytic system. After passive penetration into the host cell, the trypomastigote form of the parasite differentiates into the amastigote form, divides actively and then this is followed by a release of the trypomastigote forms, thereby causing a new cell invasion.

The vector insects will complete the parasitic cycle by ingesting, during a blood meal, the trypomastigote forms in the host. The latter differentiate into epimastigote forms in the vector's middle intestine and finally into the infectious metacyclic trypomastigote forms in the posterior intestine.

Two phases can be distinguished in the Chagas disease: the acute phase and the chronic phase. The acute phase occurs after a transfusional, congenital, or vectorial type contamination and lasts for a few weeks. It is characterized by a large number of parasites circulating in the blood and corresponds to an exponential division of the protozoan. The acute phase is most often asymptomatic. However, in infants contaminated by their mother, the acute phase, which is marked by an acute cardiopathy, may be critical. The chronic phase may extend over many years. In some individuals, this phase is asymptomatic. On the other hand, other patients have tissue lesions in the heart or digestive type manifestations. In any case, clinical diagnosis must always be confirmed by tests for the detection either of antibodies directed against the parasitic antigens, or of the parasite itself.

This disease is becoming a worldwide problem because of the contamination through blood transfusion. It has therefore become essential to have available diagnostic tests which make it possible to determine the presence of the parasite in individuals. Various serological tests are avalable, such as direct agglutination, indirect immunofluorescence (IIF), complement fixation tests (CFR), and ELISA tests (Enzyme Linked Immunosorbent Assay). The *Trypanosoma cruzi* antigens currently used for the serological tests are obtained from a total lysate or from partially purified protein fractions of the noninfectious stage of the parasite. However, these fractions do not allow antigens to be obtained in sufficient quantity and quality for the production of a reliable serological diagnostic test. Furthermore, the complexity of the parasite and the strain-to-strain antigenic polymorphism introduce an additional difficulty in the reproducibility of the different preparations. Finally, there are many risks of cross-reactivity with other protozoa, more particularly with the family Leishmania and *Trypanosoma rangeli*, a nonpathogenic parasite.

In order to solve these various problems, it was envisaged to produce a serological diagnostic kit composed of recombinant proteins which would be highly sensitive and specific for *Trypanosoma cruzi*.

Various research groups have screened libraries for expression of *Trypanosoma cruzi* genomic DNA or complementary DNA in the vector λgt11, using sera from patients suffering from Chagas disease. The λgt11 phage allows the insertion of foreign DNA of a maximum size of 7 kb into the EcoRI site localized in the lacZ gene, under the control of the lac promoter. The product obtained is a recombinant protein fused with beta-galactosidase, which is inducible by IPTG (isopropyl beta-D-thiogalactoside).

Various *Trypanosoma cruzi* genes, encoding proteins recognized by the Chagasic sera were thus characterized (Moncayo and Luquetti, 1990 and Levin et al. (1991), FEMS Microbiol. Immunol. 89: 11–20). Among the recombinant antigens described, the H49 antigen may be mentioned (Paranhos et al., 1994 (1)). However, this antigen does not allow a serological detection sensitivity of 100% of the patients in the acute or chronic phase. It was therefore envisaged to combine the H49 antigen with the CRA antigen (Cytoplasmic Repetitive Antigen) (Lafaille et al., (1989) (2)) but still without solving this problem.

SUMMARY OF THE INVENTION

The present inventors have identified and obtained a new genetic material encoding a new protein, its fragments, and antigenic determinants recognized by anti-*Trypanosoma cruzi* antisera, which makes it possible to overcome the above-mentioned disadvantages. The genetic material may be used to produce proteins or polypeptides for the production of diagnostic tests, or for the preparation of vaccinal or pharmaceutical compositions, or may itself either be used as a probe, or for the determination of specific probes which can be used in nucleic acid hybridization tests for the detection of *Trypanosoma cruzi* infections. Likewise, the protein or any corresponding polypeptide may be used for the production of antibodies specific for the parasite, for diagnostic or passive protection purposes.

DETAILED DESCRIPTION OF THE INVENTION

The new genetic material is designated Tc100 and it encodes a protein designated PTc100 by the applicant. The new genetic material and protein have also been designated Tc40 and PTc40, respectively, by the applicant.

Consequently, the subject of the present invention is a DNA or RNA molecule consisting of at least one strand comprising a nucleotide sequence represented by the identifier SEQ ID No.1, or a sequence complementary or antisense or equivalent to said sequence identified by the identifier SEQ ID No.1, and especially a sequence having, for any succession of 100 contiguous monomers, at least 50%, preferably at least 60%, or more preferably at least 85% homology with said sequence.

The invention moreover relates to DNA or RNA fragments whose nucleotide sequence is identical, complementary, antisense, or equivalent to any one of the following sequences:

that starting at nucleotide 1232 and ending at nucleotide 2207 of SEQ ID No.1, that starting at nucleotide 1232 and ending at nucleotide 1825 of SEQ ID No.1, and that starting at nucleotide 1266 and ending at nucleotide 2207, and especially the DNA or RNA fragments whose sequence has, for any succession of 30 contiguous monomers, at least 50%, preferably at least 60%, or more preferably at least 85% homology with any one of said sequences.

The prefered DNA and RNA fragment being the 1232–1825 fragment of SEQ ID No.1, the invention relates to DNA or RNA fragments which hybridize with this fragment knowing that it is tolerated until 10% of error in bases' matching.

The DNA and RNA fragment could be of any length and be comprised in the sequence from 266 to 3010 of SEQ ID No.1, knowing that this sequence is highly specific for *Trypanosoma cruzi*. Any fragment which hybridizes with the DNA or RNA of this sequence is considered as been a specific equivalent nucleotide or deoxunucleotide sequence.

Nucleotide sequence is understood to mean either a DNA strand or its complementary strand, or an RNA strand or its antisense strand or their corresponding complementary DNAs. The DNA sequence as represented in the identifier SEQ ID No.1 corresponds to the messenger RNA sequence, it being understood that the thymine (T) in the DNA is replaced by a uracil (U) in the RNA.

A still more prefered DNA and RNA fragment is the sequence from nucleotides 1472 to 1543 of SEQ ID No.1.

According to the invention, two nucleotide sequences are said to be equivalent in relation to each other, or in relation to a reference sequence if, functionally, the corresponding biopolymers can play essentially the same role, without being identical, with respect to the application or use considered, or in the technique in which they are involved; two sequences obtained because of the natural variability, especially spontaneous mutation, of the species from which they were identified, or because of induced variability, as well as homologous sequences, homology being defined below, are especially equivalent.

Variability is understood to mean any spontaneous or induced modification of a sequence, especially by substitution and/or insertion and/or deletion of nucleotides and/or of nucleotide fragments, and/or extension and/or shortening of the sequence at at least one of the ends; a nonnatural variability may result from the genetic engineering techniques used; this variability may result in modifications of any starting sequence, considered as reference, and capable of being expressed by a degree of homology relative to the said reference sequence.

Homology characterizes the degree of identity of two nucleotide (or peptide) fragments compared; it is measured by the percentage of identity which is especially determined by direct comparison of nucleotide (or peptide) sequences, relative to reference nucleotide (or peptide) sequences.

Any nucleotide fragment is said to be equivalent to a reference fragment if it has a nucleotide sequence which is equivalent to the reference sequence; according to the preceding definition, the following are especially equivalent to a reference nucleotide fragment:

a) any fragment capable of at least partially hybridizing with the complementary strand of the reference fragment, knowing that it is tolerated until 10% of error in bases' matching.

b) any fragment whose alignment with the reference fragment leads to the detection of identical contiguous bases, in greater number than with any other fragment obtained from another taxonomic group, c) any fragment resulting or capable of resulting from the natural variability of the species, from which it is obtained, d) any fragment capable of resulting from the genetic engineering techniques applied to the reference fragment, e) any fragment, containing at least 30 contiguous nucleotides, encoding a peptide homologous or identical to the peptide encoded by the reference fragment, and/or f) any fragment different from the reference fragment by insertion, deletion, or substitution of at least one monomer, extension or shortening at at least one of its ends; for example any fragment corresponding to the reference fragment flanked at at least one of its ends by a nucleotide sequence not encoding a polypeptide.

The subject of the invention is also a protein, called PTc100 by the applicant, having an apparent molecular mass of about 100 kDa, which is recognized by anti-*Trypanosoma cruzi* antisera, or an immunological equivalent of this protein, and fragments thereof. The amino acid sequence of this protein is represented by the identifier sequence SEQ ID No.2, the sequence starting at amino acid 1 and ending at amino acid 915 of the sequence defined in the identifier SEQ ID No:2.

Immunological equivalent is understood to mean any polypeptide or peptide capable of being immunologically recognized by antibodies directed against a particular protein fragment.

The invention also relates specifically to a fragment of this protein represented by the identifier sequence SEQ ID No.2, the sequence starting at amino acid 323 and ending at amino acid 520 of the sequence defined in the identifier SEQ ID No.2.

The invention also relates specifically to the antigenic determinant or epitope of the PTc100 protein, a fragment of 25 amino acids, starting at amino acid 402 and ending at amino acid 426 of SEQ ID No.2, named S23G.

The PTc100 protein and said PTc100 fragment, as well as the S23G antigenic determinant may contain modifications, especially chemical modifications, which do not alter their antigenicity, such as for example N-terminal linkage by oxidation of serine or C-terminal linkage by cysteine function or hydrazine (see Keith Rose and al., Natural Peptides as Building blocks for the synthesis of large Protein-like Molecules with Hydrazone and Oxime Linkages. Department of Medical Biochemistry, (1996)).

PTc100 protein fragment is understood to mean any fragment of the PTc100 protein which preferably has at least the sequence from amino acid 323 to 520 of SEQ ID No. 2 and/or the S23G sequence, together with some other amino acids. It is clear that the S23G fragment contains an antigenic epitope of the PTc100 protein that reacts with antibodies generated during Chagas' disease.

Moreover, the subject of the present invention is also an expression cassette which is functional especially in a cell derived from a prokaryotic or eukaryotic organism, and which allows the expression of DNA encoding the entire PTc100 protein or a fragment thereof, in particular of a DNA fragment as defined above, placed under the control of elements necessary for its expression; said protein and said protein fragments being recognized by anti-*Trypanosoma cruzi* antisera.

Generally, any cell derived from a prokaryotic or eukaryotic organism can be used within the framework of the present invention. Such cells are known to persons skilled in the art. By way of examples, there may be mentioned cells derived from a eukaryotic organism, such as the cells derived from a mammal, especially CHO (Chinese Hamster Ovarian) cells; insect cells; cells derived from a fungus, especially a unicellular fungus or from a yeast, especially of the strain Pichia, Saccharomyces, Schizosaccharomyces and most particularly selected from the group consisting of *Saccharomyces cerevisiae, Schizosaccharomyces pombe, Schizosaccharomyces malidevorans, Schizosaccharomyces sloofiae, Schizosaccharomyces octosporus,* or other systems such as Semliki forest virus and vaccinia virus. Likewise, among the cells derived from a prokaryotic organism, there may be used, without this constituting a limitation, the cells of a strain of *Escherichia coli* (*E. coli*) or other enterobacterial cells. A large number of these cells are commercially available in collections, such as ATCC (Rockville, Md., USA) and AFRC (Agriculture & Food Research Council, Norfolk, UK). The cell may also be of the wild-type or mutant type. The mutations are described in the literature accessible to persons skilled in the art.

For the purposes of the present invention, an *E. coli* DH5α cell (marketed by the company CLONTECH under the reference: C2007-1) is used; however, other cells may be used as well.

The expression cassette of the invention is intended for the production of the PTc100 protein or for fragments of said protein, such as the PTc100 fragment and/or the S23G epitope, which are produced by the above mentioned *E. coli* cell, and which are recognized by human antisera. Such antisera are obtained from patients who have contracted a *Trypanosoma cruzi* infection recently or long ago, and contain immunoglobulins specifically recognizing the PTc100 protein and/or a PTc100 protein fragment. Of course, the PTc100 protein can also be recognized by other antibodies, such as for example monoclonal or polyclonal antibodies obtained by immunization of various species with the natural above-mentioned protein, the recombinant protein, or fragments or peptides thereof.

PTc100 protein is understood to mean the native *Trypanosoma cruzi* cytoplasmic antigen, or the antigen produced especially by the genetic recombination techniques described in the present application, or any fragment or mutant of this antigen, for exemple the GST-Tc100 recombinant protein and the BIO-S23G (Tc40) peptide, provided that it is immunologically reactive with antibodies directed against the PTc100 protein of this parasite.

Advantageously, such a protein has an amino acid sequence having a degree of homology of at least 70%, preferably of at least 85%, and most preferably of at least 95% relative to the sequence identified by the identifier SEQ ID No.2. In practice, such an equivalent can be obtained by deletion, substitution, and/or addition of one or more amino acids of the recombinant protein sequence. Such homology means that the amino acid sequence of the S23G peptide, contained in the PTc100 protein and its PTc100 protein fragment, is at least preserved in order to keep the antigenicity potentiality. It is within the capability of persons skilled in the art to perform, using known techniques, these modifications without affecting immunological recognition.

Within the framework of the present invention, the PTc100 protein and the PTc100 protein fragment can be modified in vitro, especially by deletion or addition of chemical groups, such as phosphates, sugars or myristic acids, so as to enhance its antigenic stability or the presentation of one or several epitopes, such as the S23G epitope.

The expression cassette according to the invention allows the production of a PTc100 protein (having an amino acid sequence as specified above) and fragments of said protein, fused with an exogenous element which can help its stability, its purification, its production, its presentation, or its recognition. The choice of such an exogenous element is within the capability of persons skilled in the art. It may be especially a hapten, an exogenous peptide, or a protein.

The expression cassette according to the invention comprises the elements necessary for the expression of said DNA fragment in the cell considered. "Elements necessary for the expression" is understood to mean the elements as a whole which allow the transcription of the DNA fragment into messenger RNA (mRNA) and the translation of the latter into protein.

The present invention also relates to a putative promoter, specific for *T. cruzi,* which can be used in an expression cassette for eukaryotic expression of genes. Probes could also be defined in this region to detect the parasite.

The present invention also extends to a vector comprising an expression cassette according to the invention. This may be a viral vector and especially a vector derived from a baculovirus, more particularly intended for expression in insect cells, or an adenovirus-derived vector for expression in mammalian cells. It may also be an autonomously replicating plasmid vector and in particular a multiplicative vector.

The present invention also relates to a cell derived from a prokaryotic or eukaryotic organism, comprising an expression cassette, either in a form integrated in the cellular genome, or inserted in a vector which can be maintained as an extra-genomic entity. Such a cell was previously defined.

The subject of the present invention is also a process for preparing a PTc100 protein, or fragments of said protein, according to which:

(i) a cell derived from a prokaryotic or eukaryotic organism, comprising the expression cassette according to the invention, is cultured under appropriate conditions; and (ii) the expressed protein derived from the above mentioned organism is recovered.

The present invention also relates to one or more peptides, whose amino acid sequence corresponds to a portion of the sequence of the PTc100 protein and exhibits, alone or as a mixture, a reactivity with the entire sera from individuals or animals infected with *Trypanosoma cruzi.* The prefered portion is the PTc100 protein fragment or peptide defined above and the S23G peptide. The peptides can be obtained by chemical synthesis, lysis of the PTc100 protein, or by genetic recombination techniques.

The invention also relates to monoclonal or polyclonal antibodies obtained by immunological reaction of a human or animal organism to an immunogenic agent consisting of the natural or recombinant PTc100 protein and fragments thereof, or of a peptide, as defined above.

The present invention also relates to a reagent for the detection and/or monitoring of a *Trypanosoma cruzi* infection, which comprises, as reactive substance, a PTc100 protein as defined above, or fragments thereof, a peptide or a mixture of peptides as defined above, or at least one monoclonal or polyclonal antibody as described above. The above reagent may be attached directly or indirectly to an appropriate solid support. The solid support may be especially in the form of a cone, a tube, a well, a bead, and the like.

The term "solid support" as used here includes all materials on which a reagent can be immobilized for use in diagnostic tests. Natural or synthetic materials, chemically modified or otherwise, can be used as solid supports, especially polysaccharides such as cellulose-based materials, for example paper, cellulose derivatives such as cellulose acetate and nitrocellulose; polymers such as vinyl chloride, polyethylene, polystyrenes, polyacrylate or copolymers such as polymers of vinyl chloride and propylene, polymers of vinyl chloride and vinyl acetate; styrene-based copolymers, natural fibers such as cotton and synthetic fibers such as nylon; and magnetic particles. Preferably, the solid support is a polystyrene polymer or a butadiene/styrene copolymer. Advantageously, the support is a polystyrene or a styrene-based copolymer comprising between about 10 and 90% by weight of styrene units.

The binding of the reagent onto the solid support may be performed in a direct or indirect manner. Using the direct manner, two approaches are possible: either by adsorption of the reagent onto the solid support, that is to say by noncovalent bonds (principally of the hydrogen, Van der Waals or ionic type), or by formation of covalent bonds between the reagent and the support. Using the indirect manner, an "anti-reagent" compound capable of interacting with the reagent so as to immobilize the whole onto the solid support can be attached beforehand (by adsorption or covalent bonding) onto the solid support. By way of example, there may be mentioned an anti-PTc100 antibody, on the condition that it is immunologically reactive with a portion of the protein different from that involved in the reaction for recognizing the antibodies in the sera; a ligand-receptor system, for example by grafting onto the PTc100 protein a molecule such as a vitamin, and by immobilizing onto the solid phase the corresponding receptor (for example the biotin-streptavidin system). Indirect manner is also understood to mean the preliminary grafting or fusion by genetic recombination of a protein, or a fragment of this protein, or of a polypeptide, to one end of the PTc100, protein, and the immobilization of the latter onto the solid support by passive adsorption or covalent bonding of the protein or of the polypeptide grafted or fused.

The invention also relates to a process for the detection and/or monitoring of a *Trypanosoma cruzi* infection in a biological sample, such as blood serum or plasma, urine, saliva, or tear samples from an individual or an animal likely to have been infected with *Trypanosoma cruzi*, characterized in that said sample and a reagent as defined above are placed in contact, under conditions allowing a possible immunological reaction, and the presence of an immune complex with said reagent is then detected.

By way of non-limiting example, there may be mentioned the sandwich-type detection process in one or more stages, as especially described in patents FR 2,481,318 and FR 2,487,983, which consists of reacting a first monoclonal or polyclonal antibody specific for a desired antigen, attached onto a solid support, with the sample, and in revealing the possible presence of an immune complex thus formed using a second antibody labelled by any appropriate marker known to persons skilled in the art, especially a radioactive isotope, an enzyme, for example peroxidase or alkaline phosphatase and the like, using so-called competition techniques well known to persons skilled in the art.

The subject of the invention is also an active immunotherapeutic composition, especially a vaccine preparation, which comprises as active ingredient, a natural or recombinant PTc100 protein or fragments thereof, or the peptides identified above, the active ingredient being optionally conjugated with a pharmaceutically acceptable carrier, and optionally an excipient and/or an appropriate adjuvant.

The present invention also covers a pharmaceutical composition intended for the treatment or for the prevention of a *Trypanosoma cruzi* infection in man or in an animal, comprising a therapeutically effective quantity of an expression cassette, a vector, a cell derived from a prokaryotic or eukaryotic organism as defined above, a PTc100 protein according to the invention, or fragments thereof, or the peptide identified above, or an antibody of the invention.

The subject of the present invention is also probes and primers specific for *T. cruzi*, and their uses in diagnostic tests.

The term probe as used in the present invention refers to a DNA or RNA containing at least one strand having a nucleotide sequence which allows hybridization to nucleic acids having a nucleotide sequence as represented by the identifier SEQ ID No.1, or a complementary or antisense sequence, or a sequence equivalent to said sequence, and especially a sequence having, for any succession of 5 to 100 contiguous monomers, at least 50%, preferably at least 60%, or more preferably at least 85% homology with SEQ ID No.1, with fragments thereof, or with a synthetic oligonucleotide allowing such a hybridization, nonmodified or comprising one or more modified bases such as inosine, 5-methyldeoxycytidine, deoxyuridine, 5-dimethylaminodeoxyuridine, 2,6-diaminopurine, 5-bromodeoxyuridine or any other modified base. Likewise, these probes may be modified at the level of the sugar, namely the replacement of at least one deoxyribose with a polyamide (P. E. NIELSEN et al. (1991) (13)), or at the level of the phosphate group, for example its replacement with esters, especially chosen from esters of diphosphate, of alkyl and arylphosphonate and of phosphorothioate.

The probes may be much shorter than the sequence identified in the identifier SEQ ID No.1. In practice, such probes comprise at least 5 monomers, advantageously from 8 to 50 monomers, having a hybridization specificity, under defined conditions, to form a hybridization complex with DNA or RNA having a nucleotide sequence as defined above. The conditions are well-known and/or easily determined by those of skill in the art.

A probe according to the invention can be used for diagnostic purposes, such as primer for amplification of biological material, as capture and/or detection probe, or for therapeutic purposes. The capture probe can be immobilized on a solid support by any appropriate means, that is to say directly or indirectly, for example by covalent bonding or passive adsorption. The detection probe is labelled by means of a marker chosen from radioactive isotopes, enzymes especially chosen from peroxidase and alkaline phosphatase, and those capable of hydrolyzing a chromogenic, fluorigenic, or luminescent substrate, chromophoric chemical compounds, chromogenic, fluorigenic, or luminescent compounds, nucleotide base analogs, and biotin.

The probes of the present invention which are used for diagnostic purposes can be used in any known hybridization techniques, and especially the so-called "Dot-Blot" technique (Maniatis et al. (1982) (14)), Southern Blotting technique (Southern E. M. (1975) (15)), Northern Blotting technique, which is a technique identical to the Southern Blotting technique but which uses RNA as target, sandwich technique (Dunn A. R. et al. (1977) (16)). Advantageously, the sandwich tech-nique is used which comprises a specific capture probe and/or a specific detection probe, it being understood that the capture probe and the detection probe must have a nucleotide sequence which is at least partially different.

Another application of the invention is a therapeutic probe for treating infections due to *Trypanosoma cruzi,* said probe being capable of hybridizing in vivo with the DNA or RNA of the parasite to block the translation and/or transcription and/or replication phenomena.

A primer is a probe comprising 5 to 30 monomers, having a hybridization specificity, under predefined conditions, for the initiation of an enzymatic polymerization, for example in an amplification technique such as PCR (Polymerase Chain Reaction), in an elongation process such as sequencing, in a reverse transcription method and the like. Such predefined conditions are well-known and/or easily determined by those of skill in the art.

A preferred probe or primer will contain a nucleotide sequence chosen from the sequences SEQ ID No.3, SEQ ID No.4, SEQ ID No.5, SEQ ID No.6 and SEQ ID No.7.

The invention also relates to a reagent for detecting and/or identifying *Trypanosoma cruzi* in a biological sample, comprising at least one probe as defined above, and in particular a capture probe and a detection probe, either or both corresponding to the above definition.

The invention therefore provides a process for selectively detecting and/or for identifying *Trypanosoma cruzi* in a biological sample, according to which the RNA, extracted from the parasite and optionally denatured, or the DNA, denatured extract, or the DNA obtained from reverse transcription of the RNA, is exposed to at least one probe as defined above and the hybridization of said probe is detected.

BRIEF DESCRIPTION OF THE FIGURES

The invention will be understood more clearly upon reading the detailed description below which is made with reference to the accompanying figures in which:

FIG. 5 depicts:

Figure 1:
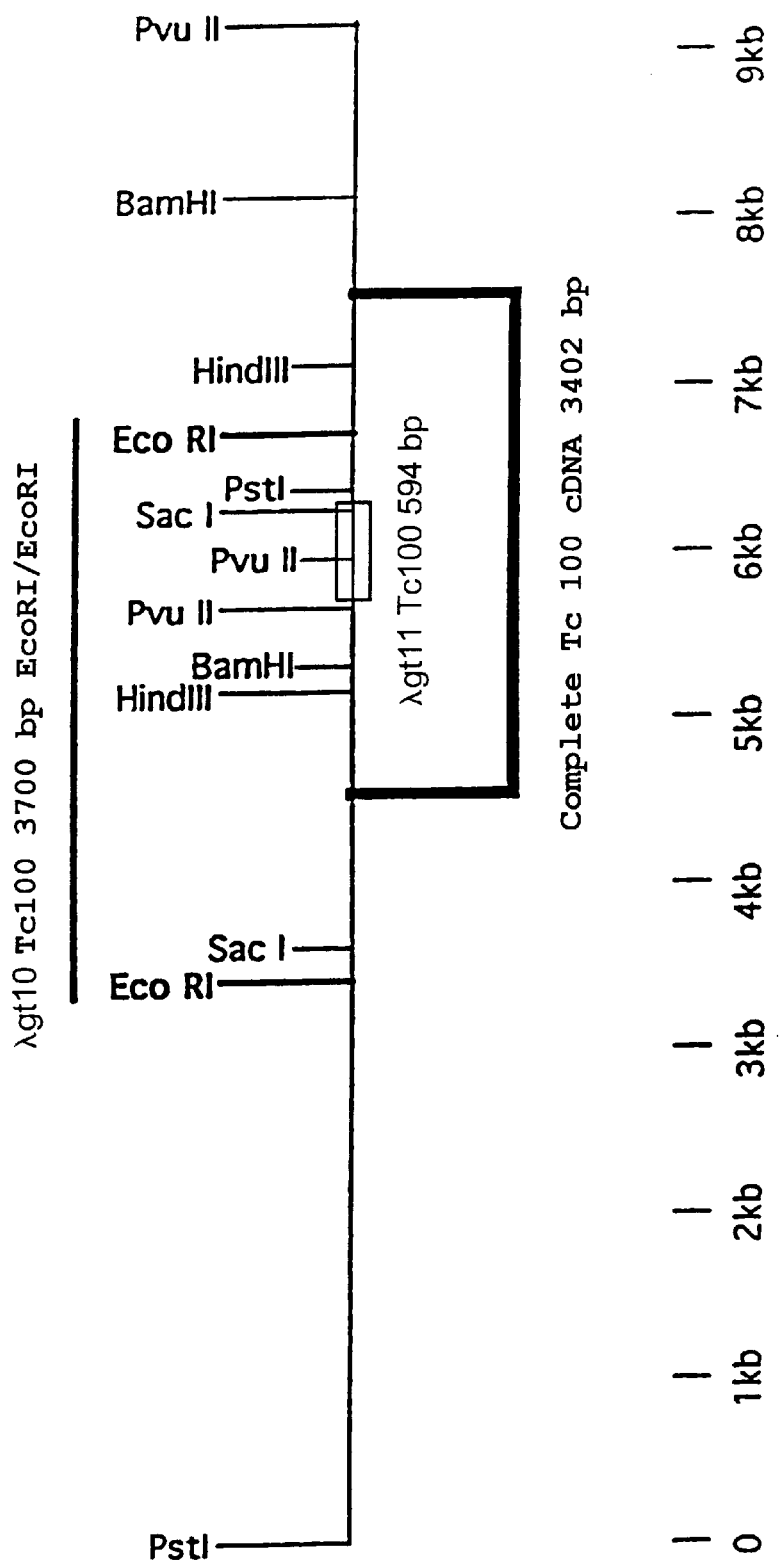
FIG. 1 depicts the restriction map of the Tc100 gene, which map is deduced by Southern blotting of different fragments obtained after digestion of *Trypanosoma cruzi* DNA with restriction endonucleases.

(A) Southern blot analysis of Tc100 gene in the G strain. 5 µg of *T. cruzi* DNA were restricted with (1) HaeIII, (2) EcoRI/HaeIII, (3) EcoRI, (4) EcoRI/PstI, (5) PstI, (6) PvuII, (7) SacI, and (8) PvuII/SacI, and subjected to Southern blot analysis using the 597-bp Tc100 probe.

(B) Restriction map of the gene locus Tc100, deduced from the combination of many analyses by Southern blot. (Ps): PstI, (E): EcoRI; (S): SacI; (D): DraI; (H): HindIII; (B): BamHI; (Ha): HaeIII; (P): PvuII; (A): AccI. The striped box represents the insert of 594 bp of the isolated λgt11-Tc100 clone.

Figure 6B:
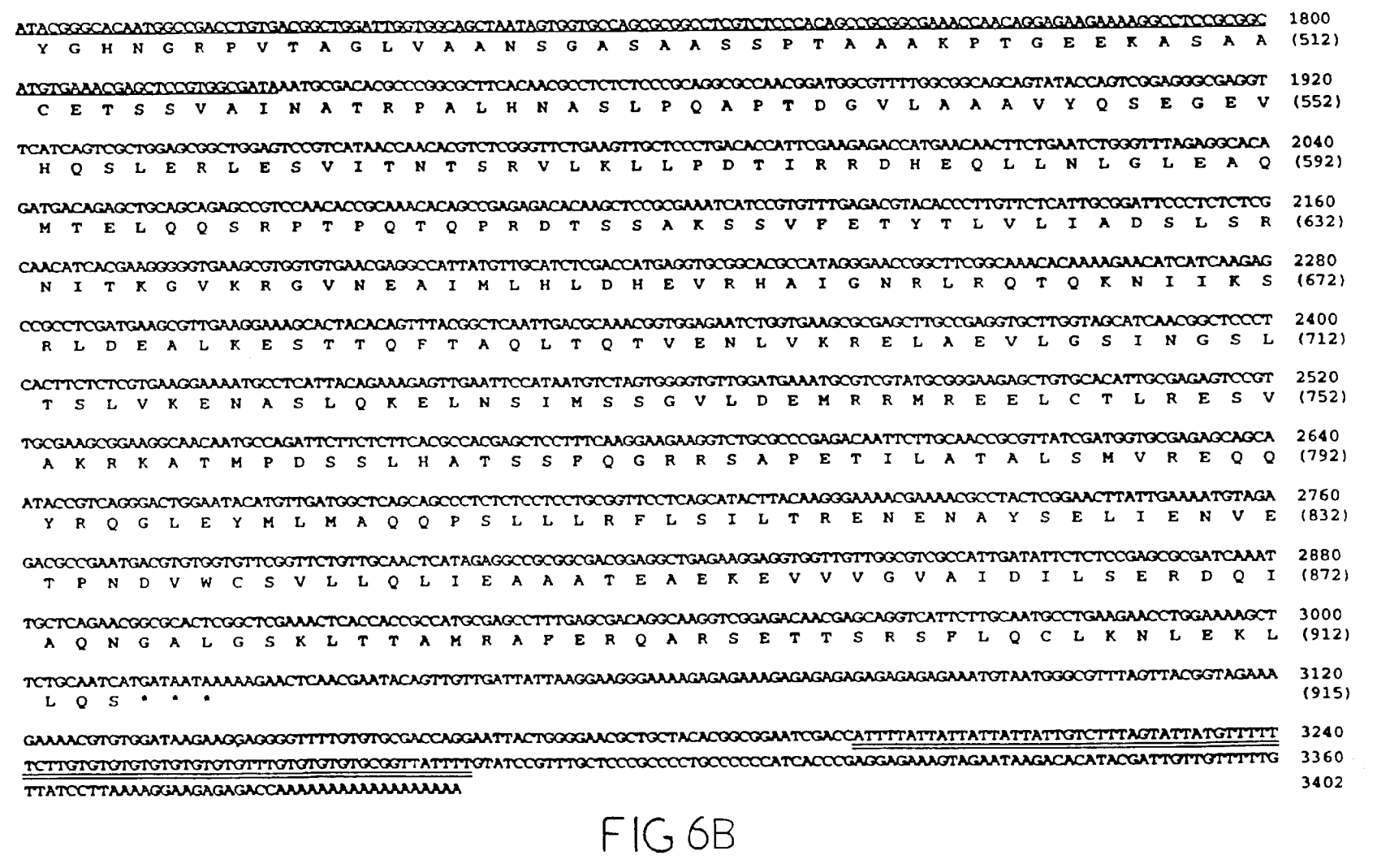

FIG. 6 depicts the nucleotide (SEQ ID NO.1) and deduced amino acid (SEQ ID NO.2) sequences of Tc100 cDNA. The asterisk at the end of the adenine segments and the "T- and GT-rich" regions are double-underlined. The complete consensus SL is dotted-underlined.

FIG. 7 depicts:

(A) Shematic representation of the Tc100 λgt10 and λgt10 genomic clones. The 594-bp and 3.7-kb EcoRI Tc100 clones are represented by a striped box and a bold line, respectively.

(B) Nucleotide sequence (SEQ ID NO.17) of the 5' region of the λgt10-Tc100 clone of 3.7 kb (GenBank accession number TCU96914). The sequence of the protein corresponding to the longest open reading frame is indicated (SEQ ID NO.18). The promotor sequence is underlined and the sites of fixation of transcription factors are indicated in bold characters; the initial site of the transcription is noted (+1). The undetermined nucleotide bases are noted N.

Figure 8:
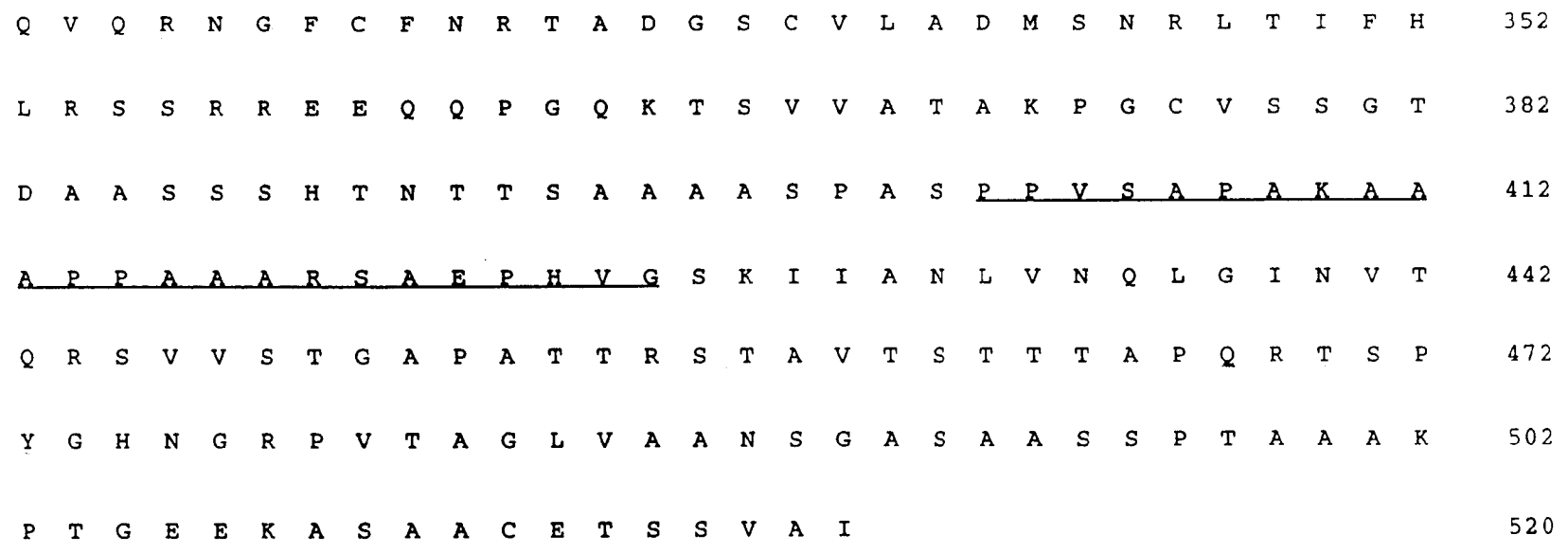

FIG. 8 depicts the localization of the human antigenic determinant in the amino acid sequence of the λgt11-Tc100 (SEQ ID NO.19). The numbering of amino acids is the one of the Tc100 protein deduced from the translation of the Tc100 cDNA. The sequence of the antigenic determinant is underlined (SEQ ID NOs. 8–16).

FIG. 9(A) depicts the in vitro transcription and translation of Tc100 cDNA. The in vitro translation labelled products of the Tc100 cDNA, cloned into pSP64 poly(A) vector dowstream of the SP6 promotor were analyzed by SDS-PAGE (1), Western blotted, and probed with a guinea pig anti-GST serum (2) and the guinea pig anti-GST-Tc100 serum (3). Size markers, shown on the left, are in kilodaltons (kDa).

FIG. 9(B) depicts the reactivity of the recombinant protein GST-Tc100 with human chagasic sera. GST-affinity purified proteins after IPTG induction of recombinant pGEX-Tc100(4) and nonrecombinant pGEX (2) were separated by 12% SDS-PAGE, Western blotted, and probed with a pool of human chronic chagasic sera. Size markers are shown on the left.

FIG. 10 depicts the serological evaluation of the BIO-S23G (Tc100) peptide in an indirect ELISA assay. Distribution of the DO values was obtained in relation to the populations of sera tested. The box plots indicate for each population of tested sera the distribution and the medium OD492nm value. The five horizontal lines of the boxes correspond to the 10, 25, 50 (medium), 75, and 90 percentiles. The values on both sides of 10 and 90 percentiles are experimental points (circles).

A corresponds to patients suffering from chronic Chagas' disease (n=184)

B corresponds to normal serum (n=63)

C corresponds to patients suffering from toxoplasmosis (n=7)

D corresponds to patients suffering from visceral-leishmaniasis (n=26)

E corresponds to patients suffering from mononucleosis (n=5)

F corresponds to patients presenting anti-nuclear antibodies (n=5)

G corresponds to patients suffering from filariosis (n=8).

MATERIALS AND METHODS USED IN THE FOREGOING EXAMPLES

*Trypanosoma cruzi* epimastigotes and metacyclic trypomastigotes were grown in liver infusion tryptose (LIT) liquid medium supplemented with 10% heat-inactivated fetal calf serum at 28° C. without shaking. Cell culture trypomastigotes and amastigotes were obtained from infected monolayers of Vero and HeLa cells. *E. coli* DH5α (Gibco BRL, France) strain was used for cloning and also for expression of fusion protein in plasmid pGEX (Pharmacia Biotech, France) whereas Y1090 strain was used for grouth and expression of phage λgt11. Phage λgt10 (Amersham, France) was grown in *E. coli* Y1089 strain.

DNA and RNA were isolated from *T. cruzi* axenic cultures by conventional protocols (see Maniatis T et al., Molecular Cloning, A Laboratory Manual, Cold Spring Harbor Laboratory, Cold Spring Harbor, N.Y., 1989). The recombinant clone Tc100 was isolated from a *T. cruzi* (G strain) genomic expression library screened with a pool of chronic chagasic sera (see Ozaki et al, Plaque antibody selection: rapid immunological analysis of a large number of recombinant phage clones positive to sera against *Plasmodium falciparum* antigens. J Immunol Methods 1986; 89:213–9). The insert from the purified original DNA clone was subcloned into the pUC19 plasmid (Gibco BRL) for sequence analysis, and into the pGEX expression plasmid to produce a fusion protein with the *Schistosoma japonicum* glutathione S-transferase (GST-Tc100) induced by isopropyl-β-D-thiogalactopyranoside.

Sera samples were collected from patients with chronic Chagas' disease diagnosed by serological methods and clinical symptoms. Serological analyses were performed by indirect immunofluorescence (ImmunoCruzi, Biolab-Mérieux, Brazil) and ELISA (BioELISAcruzi, Biolab-Mérieux, Brazil). Antibodies against the GST protein and the GST-Tc100 fusion protein were raised in guinea pigs by injecting the partially purified non recombinant and recombinant antigens extracted from polyacrylamide gels.

The GST and GST-Tc100 proteins were induced and purified onto Glutathione Sepharose 4B (Pharmacia LKB Biotechnology, France) in the presence of 1 mM phenylmethylsulfonyl fluoride. Parasites were lysed in presence of a solution containing 150 mM Nacl/10 mM Tris-Hcl, pH 7.5/1 mM EDTA/1% Nonidet-P40/1 mM phenylmethylsulfonyl fluoride/1 mM N-α-Tosyl-L-lysine-chloromethyl ketone/2 U ml-1 aprotinin/25 μg ml-1 leupeptine/25 μg ml-1 antipain (Boehringer Mannheim, France). The parasite lysate was incubated at 4° C. for 30 min, centrifuged for 10 min at 18000×g at 4° C. This supernatant was used directly in the immunoblotting study. SDS-polyacrylamide gel electrophoresis (SDS-PAGE) was performed with parasites and bacterial lysates in 10 or 12% gels in the Laemmli buffer system (see Laemmli UK, Cleavage of structural proteins during the assembly of the head of bacteriophage T4. Nature 1970; 227:680–5). Immunoblotting was carried out by the method of Towbin et al. (see Towbin et al., J. ElectrophoreticProc Natl Acad Sci USA 1979; 76:4350–4). Bound antibodies were revealed either with goat anti-human IgG coupled to alkaline phosphatase (Jackson ImmunoResaerch Laboratories) or with [125I]protein A (Amersham, France).

For intracellular staining of parasites, Vero cells grown on glass cover slips were infected with *T. cruzi*. The immunofluorescence reaction was carried out at 72–96 h postinfection, as previouly described using GST-Tc40 specific antibodies raised in guinea pig (see Cotrim PC et al., J. Expression in *Escherichia coli* of a dominant immunogen of *Trypanosoma cruzi* recognized by human chagasic sera. J Clin Microbiol 1990; 28: 519–24).

To clone the Tc100 cDNA, *T. cruzi* mRNA, G strain, was first reverse transcribed using random hexanucleotide primers, and then amplified by the polymerase chain reaction (PCR). The 5' portion was generated using a sense primer-SL (5'-AACGCTATTATTAGAACAGTT-3') (SEQ ID No.3) deduced from *T. cruzi* spliced leader (SL) sequence (see Parsons M et al., Trypanosom mRNAs share a common 5' spliced leader sequence. Cell 1984; 38: 309–16) and a reverse primer-1 (5'-TGCAGCAGCAGCGGCAGAAGT-3') (SEQ ID No.4) from Tc100 original sequence corresponding to nucleotides 1442–1459 of the Tc100 cDNA). The central region was obtained using a sense primer-2 (5'-CAGCCGACGGTAGCTGCGTCCT-3') (SEQ ID No.5) from Tc100 original sequence, corresponding to nucleotides 1266–1287 and an antisense primer-3 (5'-ACATAATGGCCTCGTTCACAC-3')(SEQ ID No.6) corresponding to nucleotides 2187–2207 of the Tc100 cDNA. To clone the 3' Tc40 cDNA ends, *T. cruzi* polyadenylated RNA, G strain, was converted into single-stranded cDNA according to the 3' rapid amplification of cDNAs ends (RACE) protocol (see Frohman MA et al., Rapid production of full-length cDNAs from rare transcripts: amplification using a single gene-specific oligonucleotide primer. Proc Natl Acad Sci USA 1988; 85:8998–9002), using a hybrid (dT) 17-adapter primer [(dT)17-AD]. The cDNA was amplified by PCR using a gene specific sense primer (5'-CGAAGAGACCATGAACAACTT-3') (SEQ ID No.7) corresponding to nucleotide positions 1997–2017 of Tc100 cDNA, and the adapter primer-AD. The sequence of primers numbered 3 and 4 were obtained from a specific Tc100 clone isolated from a 3.7-kb EcoRI λgt10 genomic *T. cruzi* library which hybridized with Tc100 original insert. The PCR experiments were performed for 35 cycles of 1 min at 94° C., 1 min at 50° C., 1 min at 72° C. followed by extension of 72° C. for 7 min, using 50 pmol of each primer and 100 ng *T. cruzi* single strand cDNA. The Taq polymerase used was obtained from Perkin Elmer Cetus, France. The PCR products that hybridized to the Tc100 original clones were cloned into the pCRII vector using TA cloning kit for PCR products (InVitrogen, San Diego, Calif.) and sequenced.

The Tc100 complete open reading frame (ORF) was obtained after assembling the 5', central, and 3' regions obtained by PCR, as described above. The sense primer sequence included the Tc100 "Kozak" consensus and the AUG start, while the antisense primer contained the three consecutive Tc100 stop codons. The PCR products were cloned into the pSP64 Poly(A) vector (Promega, Madison, Wis.), downstream of the SP6 RNA polymerase promotor and were in vitro transcribed and translated using the TNT Coupled Transcription/Translation System (Rabbit reticulocytes Lysate, Promega). The translated 35S-labeled products were separated by SDS-PAGE as described above.

The nucleotide sequence of the plasmid inserts was determined by double stranded sequencing according to the dideoxynucleotide chain termination method (see Sanger et al., DNA sequencing with chain-terminating inhibitors. Proc Natl Acad Sci USA 1977; 74:5463–7), using Sequenase (Amersham, US Biochemical, France). The Tc100 sequence analysis was carried out using the MacVector 4.5 software (Kodak). The sequence was also compared, both at the nucleotide and at the protein level, to all major sequence databases (BLASTN, BLASTP, TBLASTN). The databases were provided by the NCBI GENINFO(R) Expermental BLAST Network Service.

DNA restriction fragments were radiolabeled with ($\alpha$-$^{32}$P] dATP using a random primer DNA labelling kit (Boehringer Mannheim). Northern and Southern blots were prepared using standard methods. Hybridizations, either for DNA or RNA analysis were performed overnight at 42° C. in 6×SSC (1×SSC is 0.15 M NaCl/0.015 M sodium citrate, pH 7.5)/ 5×Denhardt's solution (1×Denhardt's solution: Ficoll 0.2 mg ml-1/polyvinylpyrrolidone 0.2 mg ml-1/bovine serum albumin 0.2 mg ml-1)/50% formamide/0.5% SDS/100 µg ml-1 sonicated herring sperm DNA. After hybridization with Tc100 probe, filters were washed in 2×SSC/0.1% SDS at room temperature for 15 min, then in 0.1×SSC/0.5% SDS at 37° C., for 30 min and, finally at 65° C., for 30 min.

The pulsed field gel electrophoresis (PFGE) samples were obtained as described in Cano M I et al., J. Molecular karyotype of clone CL brener chosen for the *Trypanosoma cruzi* genome project. Mol Biochem Parasitol 1995; 71:273–8. Agarose blocks containing 108 epimastigotes CL and G strains were prepared and strored in 0.5 M EDTA, pH 9.0. The equivalent of 107 parasites were electrophoresed at 80 V for 132 h at 13° C., with pulse times varying from 90 to 800 s. DNA chromosomal bands were transferred to nylon filters, and the blot hybridized and washed as described above.

The evaluation of the BIO-S23G peptide by the indirect ELISA process was provided on 96 wells contained plates coated with 100 µl of streptavidin in 10 µg/ml PBS overnight at 4° C. The plates were washed three times with PBS-Tween 20 at 0.05%. 100 µl of BIO-S23G peptides in 10 µg/ml PBS were adsorbed on the plates for 2 hours at 37° C. The plates were then washed. Serum was diluted 1/100 in a total volume of 100 µl and incubated for 2 hours at 37° C. After three washings, the plates were incubated for 90 minutes at 37° C. with 100 µl of anti-human IgG—goat IgG coupled with PA and diluted to 1/30000. OD was measured at 492 nm. Each sera was double tested.

The library of Tc100 peptide domains was constructed in pTOPE-T vector, according to the protocol provided by the manufacturer (Novatope Library Construction System, Novagen).

Peptides were synthetized using an Applied Biosystems 413A synthesizer, with the strategy of Emoc/tBu.

EXAMPLE 1

Isolation and Characterization of the Tc100 Recombinant Antigen

An expression library in the λgt11 vector was made directly from randomly generated fragments of *T. cruzi* nuclear DNA. Approximatively 50000 recombinant phages were screened with a pool of chronic chagasic sera and forty phages expressing *T. cruzi* antigens were detected and purified. Based on the signal intensity, clone Tc100 (594-bp) was chosen for further characterization. The Tc100 insert was subcloned into the expression vector pGEX in order to produced high amounts of the GST fusion protein in bacterial cultures induced with isopropyl-thiogalactoside. The reactivity of the fusion protein was analyzed by immunoblot assays using a pool of human chronic chagasic sera. Clone Tc100 encodes a GST fusion protein of approximately 48 kDa which strongly reacts with antibodies from chronic chagasic patients. Some proteolysis products could be observed in this antigen preparation, even in the presence of a serine protease inhibitor. In the same experiment, the non-recombinant GST protein failed to react with the human chagasic sera showing the specificity of the GST-Tc100 recombinant protein (FIG. 9B).

Figure 3:
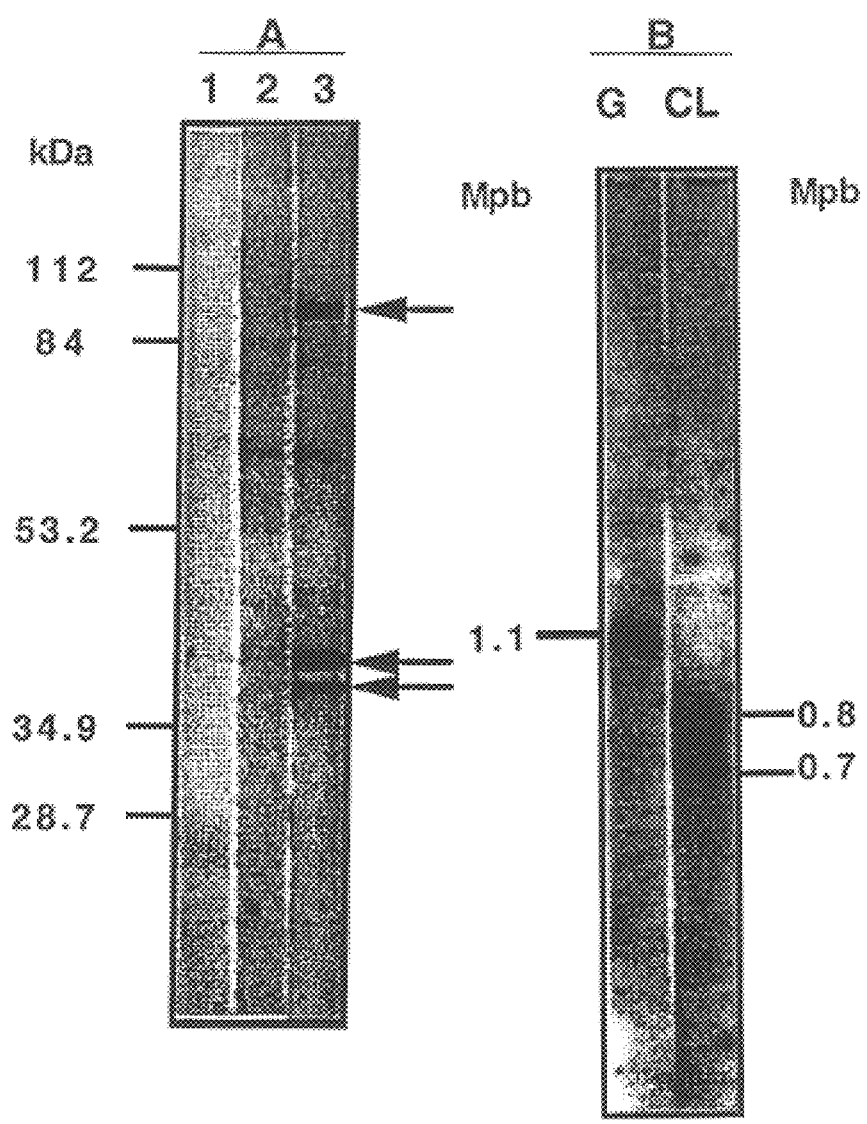
FIG. 3(A) depicts the characterization of Tc40 antigen with respect to the identification of the *T. cruzi* native antigen related to Tc40 fusion protein. Western blots of epimastigote lysates of *T. cruzi* (G strain) were incubated with the following guinea pig antisera: anti-GST serum (1), preimmune serum (2) and anti-GST-Tc100 serum (3). The arrows indicate the polypeptides specifically recognized by the anti-GST-Tc100 serum. Size markers are shown on the left.
FIG. 3(B) depicts Southern hybridization analysis showing chromosomal locations of Tc100 gene in *T. cruzi* G and CL strains. Chromosomal bands of G and CL epimastigotes were separated by pulsed field gel electrophoresis (PFGE) and analyzed by Southern blot hybridization with 594-bp Tc100 insert as probe. Molecular weights of the labelled chromosomes, in megabase pairs, corresponding to G and CL strains are noted on the left and the right of the gel, respectively.

To identify the *T. cruzi* native protein that shares common antigenic determinants with the clone Tc100, immunoblots carrying *T. cruzi* epimastigote lysates were probed with a guinea pig monospecific antiserum against the Tc100 recombinant protein. The monospecific antiserum reacted with three polypeptides of molecular masses 100, 41 and 38 kDa (FIG. 3A, lane 3). These polypeptides were also detected in comparable levels in all developmental stages of the parasite. In contrast, anti-GST control serum, such as antibodies from a preimmune animal and serum from an animal immunized with GST, failed to react with *T. cruzi* polypeptides (FIG. 3A, lanes 1 and 2). This result shows that the antigens recognized by the anti-GST-Tc100 serum are mostly related to Tc100.

The three polypeptides were detected by anti-GST-Tc100 antibodies even when the parasites were lysed in the presence of a mixture of protease inhibitors (serine, cysteine and metalloproteinases), which is normally used to protect *T. cruzi* peptides against the activity of endogenous proteases. It is noteworthy that the anti-GST-Tc100 antibodies reacted with almost the same intensity with the peptides of 100 and 41 kDa (FIG. 3A, lane 3), suggesting that they are present in equivalent amounts in the cell. Available data suggest that the peptides of molecular masses 100, 41, and 38 kDa represent different molecular entities that share common epitopes. The 41 and 38 kDa species appear to be proteolysis products of the 100 kDa protein.

The cellular location of Tc100 antigen was investigated by indirect immunofluorescence using formaldehyde-fixed parasites. The anti-Tc100 antibodies stained the cytoplasm of amastigotes and trypomastigotes. No reaction was obtained with the nucleus or the kinetoplast. Human chagasic antibodies immunopurified on the recombinant antigen also stained the cytoplasm of *T. cruzi* cells giving a fluorescence pattern similar to that obtained with the guinea pig monospecific antiserum. As expected, the anti-GST control serum did not react with *T. cruzi* intact cells (amastigotes and trypomastigotes) in indirect immunofluorescence assays. Living parasites were not labeled with anti-Tc100 antibodies, suggesting that proteins recognized by these antibodies are located in intracellular structures.

EXAMPLE 2

Cloning and Sequencing of the Tc100 Gene

Northern blots carrying mRNAs from the epimastigote stage of G and CL strains were hybridized with the insert of the Tc100 genomic clone. The probe hybridized with a transcript of about 3.9 kb in both strains. No additional bands were observed even after a longer exposure (10 days). These results indicated that the length of the gene for Tc100 was at least 3.9 kb.

Figure 2:
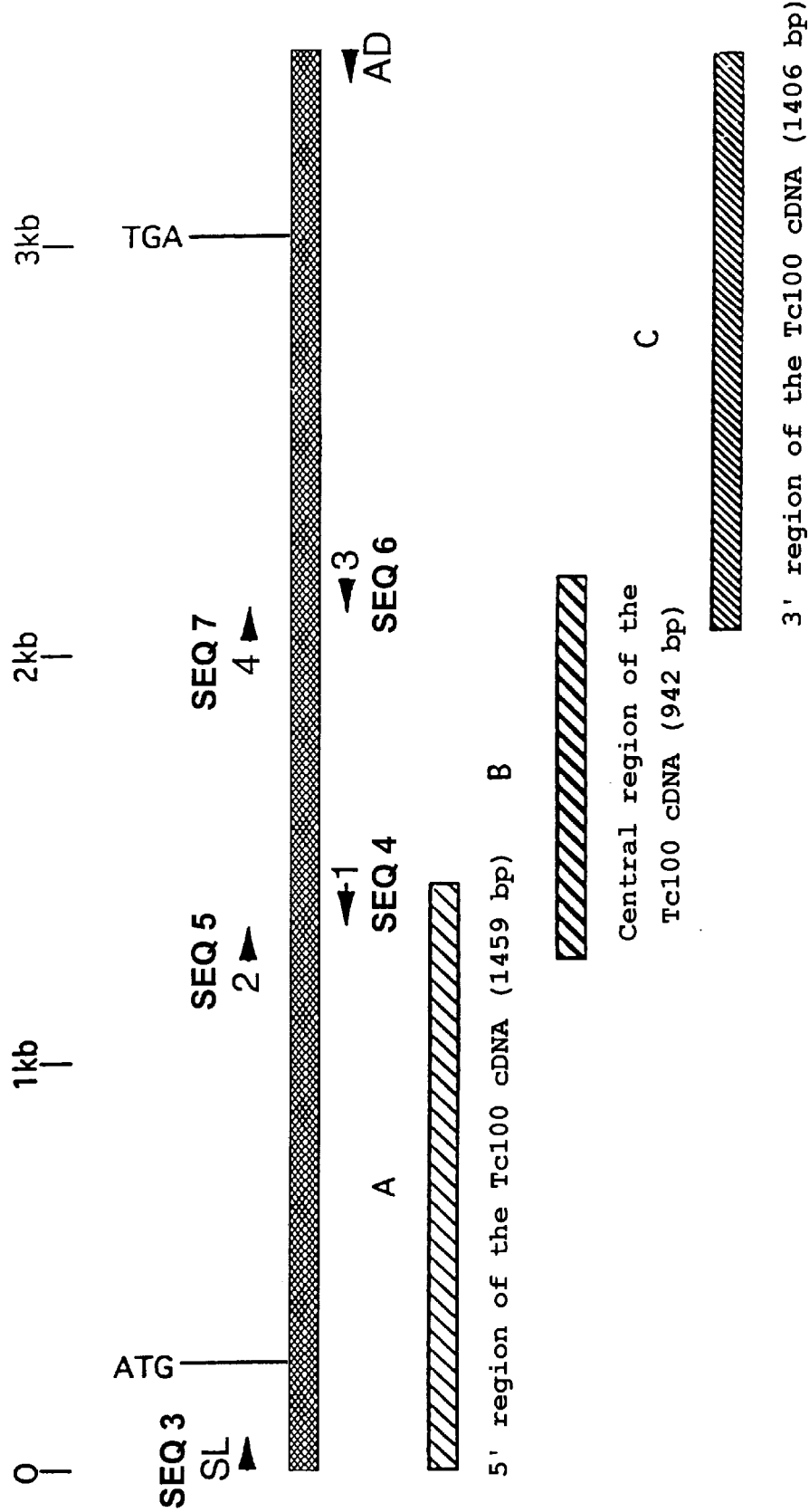
FIG. 2 is a schematic representation of the three overlapping regions corresponding to the 5', central, and 3' regions of Tc100 cDNA. The arrows noted SL, 1, 2, 3, 4, AD indicate the position of PCR primers used for amplification. The resulting full-length Tc100 cDNA is represented by a black box.

In an attempt to define the entire transcribed region of the Tc100 gene, three overlapping cDNA fragments corresponding to the 5' and 3' regions of Tc40 gene have been cloned. The cloning strategy was based on PCR amplification using a combination of specific λgt11-Tc100 (594-bp) and *T. cruzi* sequences as primers (FIG. 2). The 5' region of gene Tc100 was amplified using a pair of primers derived from SL sequence (sense) and the 594-bp genomic sequence (antisense) (FIG. 2). The amplified cDNA fragment was 1459-bp long carrying the complete 5' region of the Tc100 gene including the SL sequence. The central region of the Tc100 gene encompassing the 594-bp genomic sequence was amplified using a pair of Tc100 specific primers.

Figure 4:
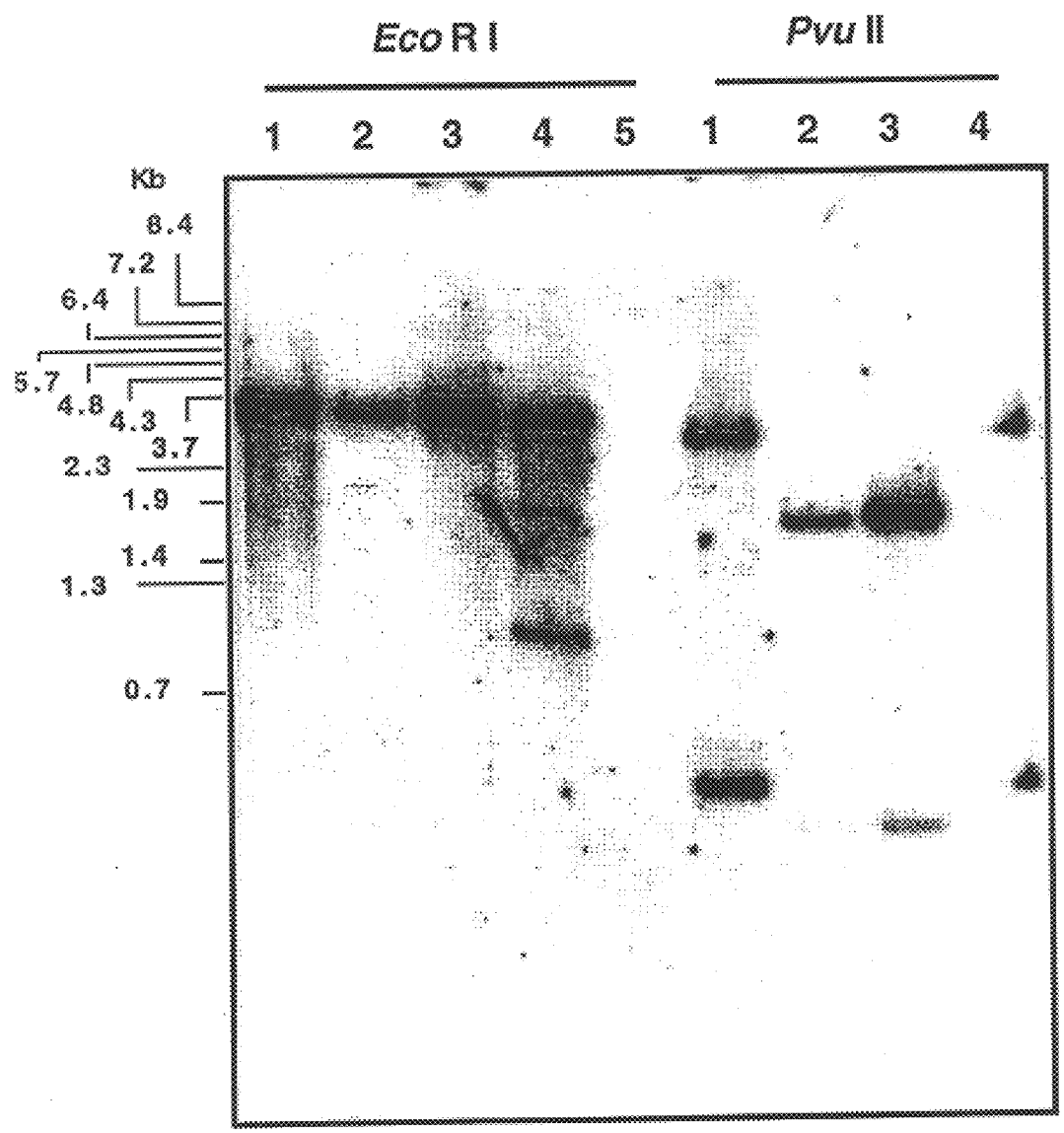
FIG. 4 depicts Southern blot analysis of the Tc100 gene. 5 µg of G (1), Y (2), CL (3), Dm30 (4) *T. cruzi* DNA and *Leishmania mexicana amazonica* (5) DNA were digested with the corresponding restriction enzymes and analyzed by Southern blotting with the radiolabelled 594-bp Tc100 insert as a probe. Size markers are shown on the left.

To obtain more information on the organization of gene Tc100, the 594-bp fragment was hybridized with a genomic Southern blot carrying *T. cruzi* DNA digested with several restriction enzymes (see FIG. 4 and 5A and 5B). A conserved EcoRI fragment of 3.7-kb was detected in all strains tested. For this reason, a *T. cruzi* genomic library was constructed in λgt10 using approximately 3.7 kb fragments obtained by complete digestion with EcoRI of *T. cruzi* (G strain) DNA and a recombinant phage carrying the expected 3.7-kb EcoRI genomic fragment was isolated after hybridization with the 594-bp clone. The region within the λgt10 recombinant clone homologous to the 594-bp sequence was identified and sequenced using specific primers. The 3' end of the 3.7-kb EcoRI fragment was also sequenced and used in the isolation of the 3' end of the transcribed region (FIG. 4, 5B and 7A). The 3' end of Tc100 gene was amplified by the 3' RACE method with a hybrid d(T)17-adaptor primer and a sense primer from an internal sequence of the 3.7-kb EcoRI genomic fragment. The generated product was 1405-bp long and presented a tail of 18 adenine residues which could correspond to the poly(A) tail. Since the Northern blot suggests that the Tc100 mRNA is 3.9 kb and the composite cDNA encompasses 3.4 kb (FIG. 6), it is possible that the 3' RACE had identified an A-rich region in the 3' untranslated region (UTR) and not identified the true poly(A) tail at the end of the mRNA that actually could have another 0.5 kb at its 3' UTR.

The complete nucleotide sequence and the predicted amino acids of the Tc100 cDNA are displayed in FIG. 6. The Tc100 cDNA is 3402 bp long with an ORF of 2745 bp encoding a polypeptide of 915 amino acids with a predicted molecular mass of approximately 100 kDa. This ORF matched with the 594 bp original insert of Tc100. It is interesting to note that no internal repeat was found in this gene, in contrast to most cloned genes encoding *T. cruzi* antigens.

The first start codon, situated 266-bp downstream of the SL sequence, complied with the nucleoside sequence frequency flanking protozoan start codon, particularly regarding the purine at position −3. The sequence upstream of the start site contains stop codons in all three frames. At the 3' end, three consecutive stop codons were detected 390-bp upstream of the putative poly-(A)-tail.

As shown above, the 3.7 kb-EcoRI genomic fragment cloned in λgt10 carries the 5' flanking region of the Tc100 gene (FIG. 1 and FIG. 7). To look for putative promoter and regulatory sequences, we have sequenced the 5' region immediately upstream from the Tc100 ORF. The 1006-bp 5' flanking sequence was analyzed with the program Proscan (version 1.7) to search for potential RNA polymerase II promoter sequences (Prestidge, D. S. (1995) Predicting Pol II promoter sequences using transcription factor binding sites. J. Mol. Biol. 245(5): 923–32). This program identified a potential TATA-box containing a promoter, with a putative transcription start site at position 609. The promoter region was predicted between position 350 and 600 (position in the GenBank accession number U96914).

The Tc100 polypeptide presents no significant similarity with other published sequences as indicated by search conducted in all major sequence databases. From the predicted amino acid sequence, in addition to 13 sites for N-glycosylation, there are 17 potential sites for myristyllation.

EXAMPLE 3

Transcription and Genomic Organization of Tc100 Gene

Northern blot analysis showed that the insert of the Tc100 genomic clone strongly hybridized to a transcript of 3.9 kb which is large enough to encode a polypeptide of 100 kDa. To further confirm the size of the Tc100 protein, full length Tc100 mRNA was transcribed and translated in vitro. Two $^{35}$S-labelled polypeptides of 100 and 80 kDa were detected (FIG. 9, lane 1), but only the 100 kDa peptide was recognized by anti-GST-Tc100 antiserum (FIG. 9, lane 3). Thus, the size of the protein translated in vitro correlated with that of the native protein found in *T. cruzi* extracts and the protein encoded by the ORF shown in FIG. 6 and 8. Clearly, it indicates that the 41 and 38 kDa peptides, also found in *T. cruzi* extracts, share common epitopes with the 100 kDa protein.

The insert of the Tc100 genomic clone was hybridized with Southern blots carrying genomic DNAs from *T. cruzi* (G, CL, Y and DM30 strains) and *Leishmania mexicana amazonensis* (FIG. 4). The probe hybridized with all *T. cruzi* DNA tested but not with Leishmania DNA, suggesting that it carries *T. cruzi* species-specific sequences. When *T. cruzi* DNA, G strain, was digested with several restriction enzymes and probed with the Tc100 genomic clone (FIG. 5A), a pattern was observed which is consistent with the presence of a few copies of Tc100 genes in the parasite genome.

Chromosomal mapping of Tc100 genes was carried out by hybridizing the 594-bp genomic fragment with the chromosomes separated by pulsed field gel electrophoresis. FIG. 3B shows the occurrence of only one hybridizing band of 1.1 Mbp in the G strain, in agreement with the above results, while the same probe hybridized with two chromosomal bands of 0.80 and 0.70 Mbp in the CL strain. These results suggested the existence of two allelic forms of Tc100 gene, on chromosomes III and IV, in the CL Brener strain (see Cano MI et al., J. Molecular karyotype of clone CL Brener chosen for the *Trypanosoma cruzi* genome project. Mol Biochem Parasitol 1995; 71: 273–8).

EXAMPLE 4

Antigenic Relevance of Tc100 Recombinant Antigen

The antigenic relevance of GST-Tc100 recombinant antigen was assessed by the immunoblot assay with a large panel of human serum samples from chronic chagasic patient (n=201), non chagasic patients (leishmaniasis, toxoplasmosis, filariasis, leprosy, mononucleosis, rheumatoid arthritis, autoimmune diseases) (n=67) and healthy individuals (n=36). The Tc100 fusion protein reacted with 92% of the serum samples from chronic chagasic patients. Out of 103 non-chagasic sera tested, only one serum sample showed a reaction with the GST-Tc100 recombinant antigen (Table 1). These result suggest that the presence of serum antibodies to the Tc100 antigen could be specifically associated with Chagas' disease.

TABLE 1

| Patients' disease | No. of individuals assayed | No. of positive individuals |
|---|---|---|
| Chagas' disease | | |
| Congenital | 9 | 8 |
| Chronic | | |
| Chronic cardiopathy | 74 | 68 |
| Digestive and cardiac/digestive forms | 6 | 5 |
| Intermediate form | 112 | 103 |
| Other diseases | | |
| Toxoplasmosis | 7 | 0 |
| Kalar-azar | 28 | 1 |
| Mucosal-Leishmaniasis | 6 | 0 |
| Filariasis | 8 | 0 |
| Leprosy | 3 | 0 |
| Mononucleosis | 5 | 0 |
| Rheumatoid Arthritis | 5 | 0 |
| Autoimmune disease | 5 | 0 |
| Normal | 36 | 0 |

It demonstrates that the gene structure of Tc100 protein does not carry a repetitive amino acid pattern found in the majority of recombinant antigens isolated by screening of *T. cruzi* expression libraries with human chagasic sera. In this context it is interesting to note that other *T. cruzi* proteins (ribosomal P proteins), which do not present repetitive motifs, are also antigenic in Chagas' disease (see Levin M J et al., The *Trypanosoma cruzi* ribosomal P protein family: classification and antigenicity. Parasitol Today 1993; 9: 381–4).

Natural humoral immune responses to many *T. cruzi* antigens appear to be largely directed to epitopes encoded by the repeat units. The strength of signals given by chronic chagasic sera in Western blot immunoassays of Tc100 recombinant protein indicates that antibodies against non-repetitive antigens are also present in the chronic phase of Chagas' disease. High antibody titers against repetitive amino acid motifs in the great majority of individuals living in endemic areas appear inconsistent with repetitive epitopes being the target of host-protective immune reponses.

Recently, several studies have demonstrated that *T. cruzi* recombinant antigens can be potentially used in the serological diagnosis of Chagas' disease (see Moncayo A et al., Multicenter double blind study for evaluation of *Trypanosoma cruzi* defined antigens as diagnostic reagents. Ment Inst Oswaldo Cruz 1990; 85: 489–95). Tc100 recombinant peptide was used in immunoblot assays to screen standard sera classified as chagasic and non-chagasic based on conventional serological tests. The sensitivity (92%) and specificity (99%) of Tc100 antigen are comparable with the other *T. cruzi* serodiagnostic tests based on recombinant antigens.

EXAMPLE 5

Identification of an Immunodominant Domain of PTc100

In order to determine more precisely the antigenic domain(s) of the PTc100 protein, an expression library of fragments of Tc100 was made from the DNA of the genomic clone λgt11-Tc100. The insert of 594 bp of the clone λgt10-Tc100 was digested with deoxyribonuclease I and populations of fragments of various sizes from 50 to 150 bp were cloned in the pTOPE-T vector. The immunologic screening of the obtained library was carried out with the pool of human chagasic serum of chronic phase. The screening of about 3000 bacterial clones with the pool of human chagasic sera led to the isolation of an identified clone.

Total protein extracts of the isolated clone and of the non-recombinant control were analyzed by immunoblotting. Fusion proteins with Protein 10 of the T7 phage (36 kDa) have been identified with the monoclonal anti-"T7.Tag ". The recombinant proteins expressed by the "human Tc100 epitope" clone are recognized with the pool of human chagasic serum from chronic phase.

The nucleotide sequence of the "human Tc100 epitope" clone was located in position 1472–1543 in the Tc100 DNA (amino acids 403 to 426 of the PTc100 protein) (FIG. 8).

The antibodies of the human chagasic sera are directed against the antigenic domain localized in position 403–426 of the PTc100 protein.

The antigenic domain determined with the antibodies from human chagasic serum present some particularities in its sequence. It presents 6 prolines, which can introduce a constraint in the polypeptide chain and thus induce a secondary or tertiary structure. Two motifs of three consecutive alanine amino acids are observed as well.

The use of peptides corresponding to the sequence of the immunodominant human domain of the PTc100 protein may eliminate problems related to the purification of the GST-Tc100 antigen as well as problems of reactivity of some serum with the GST protein.

In order to determine if the sequence of the "human Tc100 epitope" represents the major antigenic determinant of the Tc100 protein of *T. cruzi*, a peptide referred to as S23G (Tc100) presenting that sequence was syntesized. The serine in position 402 of the sequence of the PTc100 was integrated to the sequence of the peptide [S23G(Tc100) and not P22G (Tc100)] in order to allow the linking of this peptide with an amine by the intermediary of a free alcohol function at the N-terminal end of the peptide.

The S23G(Tc100) peptide corresponding to the Tc human antigenic domain has been validated in indirect standard ELISA with a pool of human chagasic serum from chronic phase and two characterized non chagasic serum. No reactivity was observed with the negative sera and with the pool of human chagasic sera from chronic phase.

The reactivity of the S23G (Tc100) peptide was checked with an inhibition test against the recombinant GST-Tc100 protein adsorbed under standard conditions on the ELISA plate. Added at 20 μg/ml to the pool of human chagasic serum, the inhibitor peptide caused inhibition of about 80% of the fixation of the anti-GST-Tc100 antibodies from the chagasic human pool. A similar result was obtained when a control recombinant GST-Tc100 antigen was added to the pool of human chagasic sera. On the other hand, no reactivity was observed with the negative tested serum. These results demonstrate clearly the reactivity of the S23G (Tc100) peptide towards the anti-Tc100 antibodies.

In order to explain the absence of reactivity of the S23G (Tc100) peptide on solid phase, the secondary structure of the S23G peptide was verified, and it shows that the S23G (Tc100) peptide presents no secondary structure, and that the human Tc100 epitope is sequential.

In order to keep the accessibility of the human Tc100 epitope, a biotin has been linked to the N-terminal end of the S23G (Tc100) peptide (BIO-S23G (Tc100)). The BIO-S23G peptide was tested in an indirect ELISA. Comparison of results obtained in an ELISA using BIO-S23G peptide and in a Western blot using GST-Tc100 antigen, as it is demonstrated in Table II, suggests that the S23G peptide contains the immunodominant epitope of the recombinant Tc100 antigen in the natural infection of *T. cruzi*.

TABLE II

| Serum | reactivity of GST-Tc100 antigen in Western blot[a] | reactivity of BIO-S23G peptide in ELISA ($OD_{492nm}$) |
|---|---|---|
| Chronic Chaga' disease | | |
| 1 | +++ | >2.5 |
| 2 | +++ | >2.5 |
| 3 | +++ | >2.5 |
| 4 | + | 0.37 |
| 5 | + | 0.37 |
| 6 | + | 0.47 |
| 7 | + | 0.68 |
| 8 | + | 2.4 |
| 9 | negative | 0.23 |
| 10 | negative | 0.7 |
| 11 | negative | 0.49 |
| 12 | negative | 0.3 |
| healthy individuals' serum | | |
| 13 | negative | 0.04 |
| 14 | negative | 0.06 |
| 15 | negative | 0.05 |

[a]crosses indicate the relative degree of reactivity of sera with the GST-Tc100 antigen.

The reactivity of the S23G (Tc100) biotinylated peptide was analyzed ELISA test using an important panel of human chagasic and non-sera from chronic phase chagasic patients (indeterminate form, cardiac and digestive forms), including more than 95% of the sera tested in Western blots on the recombinant GST-Tc100 antigen, were tested. In order to better evaluate the test specificity, the number of sera from healthy individual was increased to 63, including 40 French donor samples. The BIO S23G (Tc100) reactivity was analyzed as well on sera from patients suffering from toxoplasmosis (n=7), mucosal-leishmaniasis (n=26), mononucleosis (n=5), filariasis (n=8) and on sera from patients presenting anti-nuclear antibodies (n=5). All these sera have been tested in Western blots of the recombinant GST-Tc100 antigen. Each plate includes two negative control sera, two "treshold" anti-Tc100 control sera, previously identified in a Western blot, as well as a strong positive control anti-Tc100 sera. The distribution of the obtained values of $OD_{492}$ are presented in FIG. 10 according to the different tested populations. The discrimination between the chagasic and non-chagasic sera is satisfactory. Actually, the average of the obtained $OD_{492}$ on the whole chagasic population is 1.6+/−0.86, whereas the average of the obtained $OD_{492}$ on the whole non-chagasic population is 0.17+/−0.24. No interference is observed with sera from patients suffering from toxoplasmosis, mononucleosis, filariasis, or patients suffering from autoimmune diseases. However, among the population of sera from normal individuals, five sera from French blood donors present a weak reactivity with the BIO S23G (Tc100) peptide. Sera from patients suffering from visceral-leishmaniasis present a higher reactivity than the other populations (OD+0.39+/−0.38). The cut-off was determined as the mean of all non-chagasic populations+3 standard deviations. It was evaluated to be OD=0.

The sensitivity has been determined at 81%, and the specificity at 96% on the tested population.

Reliability may also be increased by the combination of two or more antigens to buid up a multi-antigen immunoassay. The repertoire of B-cell epitopes in a non-repetitive antigen is larger than that found in repetitive antigens. In order to improve the specificity of serodiagnostic tests, the non-repetitive antigens, such as Tc100 and/or S23G and 1F8 (see Godsel L M et al., Utility of recombinant flegellar calcium-binding protein for serodiagnosis of *Trypanosoma cruzi* infection. J Clin Microbiol 1995; 33: 2082–5 and Engeman D M et al., J Biol Chem 1989; 264: 18627–31,) should be included in the multi-antigen immunoassays.

EXAMPLE 6

Location of Ptc100 Epitope

In order to determine more pricesely the major epitope of Ptc100 protein, nine overlapping peptides of 9 to 12 amino acids, corresponding to the S23G sequence, were synthesized:

```
P1 (1–10)   SPPVSAPAKA                    (SEQ ID NO:8)
P2 (3–12)     PVSAPAKAAA                  (SEQ ID NO:9)
P3 (5–16)       SAPAKAAAPPAAA             (SEQ ID NO:10)
P4 (7–16)         PAKAAAPPAAA             (SEQ ID NO:11)
P5 (9–18)           KAAAPPAAAR            (SEQ ID NO:12)
P6 (11–20)            AAPPAAARSA          (SEQ ID NO:13)
P7 (13–24)              PPAAARSAEPHV      (SEQ ID NO:14)
P8 (15–24)                AAARSAEPHV      (SEQ ID NO:15)
P9 (17–25)                  ARSAEPHVG     (SEQ ID NO:16)
```

Reactivity of each peptide was checked with an inhibition test against the recombinant GST-Tc100 protein adsorbed under standard conditions on an ELISA plate. Added at 10 microgram/ml to the pool of human chagasic sera, two peptides (P3 (5–16) and P4 (7–16)) showed inhibition of 83 and 80%, respectively, of the fixation of the anti-GST-Tc100 antibodies from the chagasic human pool. No inhibition was observed with the other peptides. These results indicate that the major epitope of PTc100 is more precisely located at positions 406–417 of the PTc100 protein.

What is claimed is:

1. A synthetic or isolated cytoplasmic protein fragment selected from the group consisting of:
    the amino acid sequence from residue 402 to residue 426 of SEQ ID NO: 2; and
    an immunogenic fragment of said amino acid sequence comprising at least residue 408 to residue 417 of said amino acid sequence.

2. A composition comprising at least two different protein fragments according to claim 1, wherein said composition exhibits reactivity with sera from individuals or animals infected with *Trypanosoma cruzi*.

3. A reagent for detecting or monitoring a *Trypanosoma cruzi* infection, said reagent comprising a protein fragment according to claim 1.

4. A synthetic or isolated peptide molecule of *Trypanosoma cruzi*, wherein said peptide molecule contains no more than 25 amino acids and specifically binds to antibodies that specifically bind to a protein fragment consisting of the amino acid sequence from residue 402 to residue 426 of SEQ ID NO: 2.

5. The protein fragment according to claim 1, wherein said protein fragment is recognized by anti-PTc100 antibodies.

6. A reagent for detecting or monitoring a *Trypanosoma cruzi* infection, said reagent comprising a composition according to claim 2.

7. The peptide molecule according to claim 4, wherein said peptide molecule specifically binds to anti-*Trypanosoma cruzi* antisera.

8. The protein fragment of claim 1, wherein said protein fragment comprises no more than 25 amino acids.

9. The protein fragment of claim 1, wherein said protein fragment is the amino acid sequence from residue 402 to residue 426 of SEQ ID NO: 2.

10. A composition comprising at least two different peptide molecules according to claim 4, wherein said composition exhibits reactivity with sera from individuals or animals infected with *Trypanosoma cruzi*.

11. A reagent for detecting or monitoring a *Trypanosoma cruzi* infection, said reagent comprising a peptide molecule according to claim 4.

12. A reagent for detecting or monitoring a *Trypanosoma cruzi* infection, said reagent comprising a composition according to claim 10.

13. The peptide molecule according to claim 4, wherein said peptide molecule is recognized by anti-PTc100 antibodies.

14. The protein fragment according to claim 1, wherein said protein fragment is the amino acid sequence from residue 406 to residue 417 of SEQ ID NO: 2.

15. The protein fragment according to claim 1, wherein said protein fragment is the amino acid sequence from residue 408 to residue 417 of SEQ ID NO: 2.

16. The protein fragment according to claim 1, wherein said immunogenic fragment comprises at least residue 406 to residue 417 of said amino acid sequence.

17. The peptide molecule according to claim 4, wherein said peptide molecule comprises the amino acid sequence from residue 408 to residue 417 of SEQ ID NO: 2.

18. The peptide molecule according to claim 17, wherein said peptide molecule comprises the amino acid sequence from residue 406 to residue 417 of SEQ ID NO: 2.

\* \* \* \* \*

UNITED STATES PATENT AND TRADEMARK OFFICE
CERTIFICATE OF CORRECTION

PATENT NO.     : 6,403,103 B1
DATED          : June 11, 2002
INVENTOR(S)    : Glaucia Paranhos-Baccala et al.

It is certified that error appears in the above-identified patent and that said Letters Patent is hereby corrected as shown below:

<u>Title page,</u>
Item [54], please change "TRYPANOSOMA CRUZI ANTIGEN, GENE ENCODING THEREFORE, AND METHODS OF DETECTING AND TREATING CHAGAS DISEASE" to -- TRYPANOSOMA CRUZI ANTIGEN, GENE ENCODING THEREFOR, AND METHODS OF DETECTING AND TREATING CHAGAS DISEASE --;
Item [75], please change "Lyons" to -- Lyon --; and
Item [30], please change "August 12, 1995" to -- August 12, 1994 --.

Signed and Sealed this

Third Day of December, 2002

JAMES E. ROGAN
*Director of the United States Patent and Trademark Office*